US010354550B2

(12) United States Patent
Ito et al.

(10) Patent No.: US 10,354,550 B2
(45) Date of Patent: Jul. 16, 2019

(54) SWING DIAGNOSIS APPARATUS, SWING DIAGNOSIS SYSTEM, SWING DIAGNOSIS METHOD, AND RECORDING MEDIUM

(71) Applicant: SEIKO EPSON CORPORATION, Tokyo (JP)

(72) Inventors: Tsuyoshi Ito, Suwa (JP); Kenya Kodaira, Azumino (JP); Norihisa Hagiwara, Hachioji (JP); Kazuhiro Ito, Yokohama (JP)

(73) Assignee: SEIKO EPSON CORPORATION, Tokyo (JP)

( * ) Notice: Subject to any disclaimer, the term of this patent is extended or adjusted under 35 U.S.C. 154(b) by 213 days.

(21) Appl. No.: 15/211,636

(22) Filed: Jul. 15, 2016

(65) Prior Publication Data

US 2017/0028283 A1 Feb. 2, 2017

(30) Foreign Application Priority Data

Jul. 28, 2015 (JP) ................. 2015-148640

(51) Int. Cl.
*A63B 69/36* (2006.01)
*G09B 19/00* (2006.01)
*A61B 5/00* (2006.01)

(52) U.S. Cl.
CPC ........ *G09B 19/0038* (2013.01); *A61B 5/6895* (2013.01)

(58) Field of Classification Search
USPC .......................... 473/219, 221, 222, 223, 409
See application file for complete search history.

(56) References Cited

U.S. PATENT DOCUMENTS

| | | | | |
|---|---|---|---|---|
| 3,945,646 A | * | 3/1976 | Hammond | A63B 24/0003 473/223 |
| 4,137,566 A | * | 1/1979 | Haas | A63B 24/0003 273/DIG. 24 |
| 5,111,410 A | * | 5/1992 | Nakayama | A61B 5/1127 348/157 |
| 6,793,585 B1 | * | 9/2004 | Miyamoto | A63B 24/0003 473/151 |
| 7,857,708 B2 | * | 12/2010 | Ueda | A63B 24/0003 382/103 |
| 8,142,300 B2 | * | 3/2012 | Iwatsubo | A63B 24/0003 473/222 |
| 9,211,439 B1 | * | 12/2015 | Pedenko | A63B 24/0006 |
| 2002/0064764 A1 | * | 5/2002 | Fishman | A63B 24/0003 434/252 |

(Continued)

FOREIGN PATENT DOCUMENTS

| | | |
|---|---|---|
| JP | 2003-088604 A | 3/2003 |
| JP | 2004-135908 A | 5/2004 |

(Continued)

*Primary Examiner* — Nini F Legesse
(74) *Attorney, Agent, or Firm* — Oliff PLC

(57) ABSTRACT

A swing diagnosis apparatus includes a level calculation section that calculates a level on the basis of a relationship between a rotation angle about a rotation axis of an exercise appliance at a predetermined timing between the time of starting a backswing and the time of impact with a longitudinal direction of the exercise appliance as the rotation axis, and an inclination of a ball hitting portion of the exercise appliance at impact.

21 Claims, 15 Drawing Sheets

(56) References Cited

U.S. PATENT DOCUMENTS

| | | | |
|---|---|---|---|
| 2002/0077189 A1* | 6/2002 | Tuer | A63B 69/3632 473/151 |
| 2005/0215336 A1 | 9/2005 | Ueda et al. | |
| 2014/0114453 A1* | 4/2014 | Bentley | A61B 5/1122 700/91 |
| 2014/0200094 A1* | 7/2014 | Parke | A63F 13/00 473/223 |
| 2014/0379293 A1* | 12/2014 | Sato | G09B 19/003 702/141 |
| 2014/0379295 A1 | 12/2014 | Sato et al. | |
| 2015/0072797 A1* | 3/2015 | Sakyo | A63B 24/0006 473/223 |
| 2017/0028251 A1 | 2/2017 | Ito et al. | |
| 2017/0028252 A1 | 2/2017 | Ito et al. | |
| 2017/0028254 A1 | 2/2017 | Ito et al. | |
| 2017/0028282 A1 | 2/2017 | Ito et al. | |
| 2017/0036082 A1 | 2/2017 | Kodaira et al. | |

FOREIGN PATENT DOCUMENTS

| | | |
|---|---|---|
| JP | 2005-270500 A | 10/2005 |
| JP | 2015-002911 A | 1/2015 |
| JP | 2015-073821 A | 4/2015 |
| JP | 2017-023636 A | 2/2017 |
| JP | 2017-023637 A | 2/2017 |
| JP | 2017-023639 A | 2/2017 |
| JP | 2017-023640 A | 2/2017 |
| JP | 2017-023643 A | 2/2017 |
| JP | 2017-029460 A | 2/2017 |

* cited by examiner

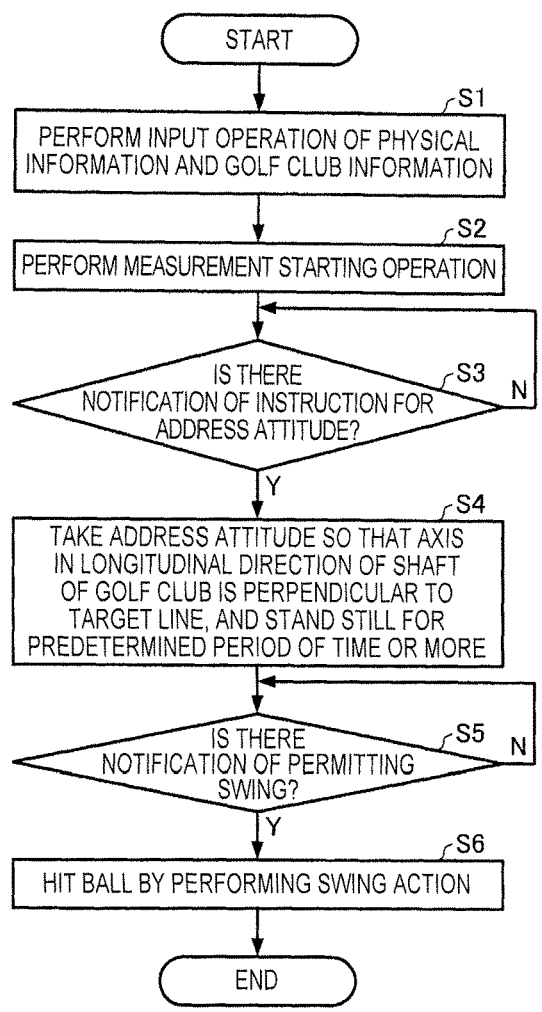

SWING ANALYSIS DATA

| SEX | MALE |
|---|---|
| TYPE OF GOLF CLUB | DRIVER |
| FACE ANGLE | 4.0deg |
| SHAFT AXIS ROTATION ANGLE AT TOP | 70.0deg |
| HEAD SPEED | 40.0m/s |

ROTATION

4POINTS / 5POINTS

SPEED

3POINTS / 5POINTS

TOTAL SCORE

70POINTS / 100POINTS

ROTATION SCORE TABLE

| ROTATION SCORE TABLE | | FACE ANGLE φ [deg] | | | | | | |
|---|---|---|---|---|---|---|---|---|
| | | CLOSE | | | SQUARE | OPEN | | |
| | | LESS THAN φ1 | φ1~φ2 | φ2~φ3 | φ3~φ4 | φ4~φ5 | φ5~φ6 | φ6 OR MORE |
| SHAFT AXIS ROTATION ANGLE $\theta_{top}$ [deg] | LESS THAN θ1 | pr1 | pr2 | pr3 | pr4 | pr5 | pr6 | pr7 |
| | θ1~θ2 | pr8 | pr9 | pr10 | pr11 | pr12 | pr13 | pr14 |
| | θ2~θ3 | pr15 | pr16 | pr17 | pr18 | pr19 | pr20 | pr21 |
| | θ3~θ4 | pr22 | pr23 | pr24 | pr25 | pr26 | pr27 | pr28 |
| | θ4 OR MORE | pr29 | pr30 | pr31 | pr32 | pr33 | pr34 | pr35 |

FIG. 14B

| TENDENCY OF IMPACT ZONE | | FACE ANGLE φ [deg] | | |
|---|---|---|---|---|
| | | CLOSE | SQUARE | OPEN |
| SHAFT AXIS ROTATION ANGLE $\theta_{top}$ [deg] | 0 | INWARD HAND-SWING | good | UPRIGHT SWAY |
| | ~60 | MIDDLE CLOSE | good | PLANE SWAY |
| | 60~ | FLAT HAND-SWING | FLAT good | FLAT SWAY |

| SPEED SCORE TABLE | | 1 POINT | 2 POINTS | 3 POINTS | 4 POINTS | 5 POINTS |
|---|---|---|---|---|---|---|
| MALE | DRIVER | LESS THAN vh1 | vh1~vh2 | vh2~vh3 | vh3~vh4 | vh4 OR MORE |
| | IRON | LESS THAN vh5 | vh5~vh6 | vh6~vh7 | vh7~vh8 | vh8 OR MORE |
| FEMALE | DRIVER | LESS THAN vh11 | vh11~vh12 | vh12~vh13 | vh13~vh14 | vh14 OR MORE |
| | IRON | LESS THAN vh15 | v15~vh16 | vh16~vh17 | vh17~vh18 | vh18 OR MORE |

FIG. 15

SWING DIAGNOSIS APPARATUS, SWING DIAGNOSIS SYSTEM, SWING DIAGNOSIS METHOD, AND RECORDING MEDIUM

BACKGROUND

1. Technical Field

The present invention relates to a swing diagnosis apparatus, a swing diagnosis system, a swing diagnosis method, and a recording medium.

2. Related Art

JP-A-2004-135908 discloses a measurement system provided with sensor means for detecting passing of a golf club head which is swung downward in order to hit a golf ball; an impact camera which captures an image of impact; a first ball measurement camera and a second ball measurement camera which are set at positions separated from each other by a predetermined distance along a flight line (flight trajectory) of a hit ball in order to capture images of the hit ball after the impact; a performance measurement device of the golf club; and a monitor which displays a movement state of the golf ball. The measurement system analyzes a movement state of the hit golf ball on the basis of the images, and displays the movement state of the golf ball as a radar chart. Therefore, according to the measurement system, it is possible to easily evaluate performance of a golf club on the basis of a movement state of the golf ball.

However, the measurement system disclosed in JP-A-2004-135908 displays a movement state of the hit golf ball, that is, data after impact, as a radar chart, and thus it is hard to understand features of a swing till the impact even if the radar chart is observed.

SUMMARY

An advantage of some aspects of the invention is to provide a swing diagnosis apparatus, a swing diagnosis system, a swing diagnosis method, and a recording medium, capable of clearly showing features of a swing till impact.

The invention can be implemented as the following forms or application examples.

Application Example 1

A swing diagnosis apparatus according to this application example includes a level calculation section that calculates a level on the basis of a relationship between a rotation angle about a rotation axis of an exercise appliance at a predetermined timing between the time of starting a backswing and the time of impact with a longitudinal direction of the exercise appliance as the rotation axis, and an inclination of a ball hitting portion of the exercise appliance at impact.

The predetermined timing may be the time at which the backswing transitions to a downswing, may be the time at which the longitudinal direction of the exercise appliance becomes a direction along a horizontal direction during the backswing, and may be the time at which the longitudinal direction of the exercise appliance becomes a direction along a horizontal direction during the downswing.

The exercise appliance is a tool used for a swing, and may be, for example, a golf club, a tennis racket, a baseball bat, or a hockey stick.

The level calculation section may calculate the level on the basis of data regarding a swing. The data regarding the swing may be, for example, measured data of acceleration or angular velocity regarding the swing, and may be analysis information including values of indexes indicating features of the swing, obtained by analyzing the measured data. Alternatively, the data regarding the swing may be data in which some or all values of indexes indicating features of the swing are pseudo-values. The data regarding the swing may be data based on an output signal from an inertial sensor measuring acceleration or angular velocity regarding the swing.

According to the swing diagnosis apparatus of this application example, since a level is calculated on the basis of a relationship between a rotation angle about a rotation axis of an exercise appliance at a desired timing during a swing, and an inclination of a ball hitting portion of the exercise appliance at impact, it is possible to grade and clearly show features of the swing till the impact.

Application Example 2

In the swing diagnosis apparatus according to the application example, the rotation angle may be an angle by which the exercise appliance is rotated about the rotation axis from the time of starting the backswing to the predetermined timing.

According to the swing diagnosis apparatus of this application example, it is possible to grade and clearly show a feature of the swing based on a relative rotation angle about the longitudinal direction of the exercise appliance at a desired timing during the swing when the time of starting the backswing is used as a reference.

Application Example 3

In the swing diagnosis apparatus according to the application example, the predetermined timing may be the time at which the backswing transitions to a downswing.

According to the swing diagnosis apparatus of this application example, it is possible to grade and clearly show a feature of the swing based on a relationship between a rotation angle about the longitudinal direction of the exercise appliance at the time of starting the downswing and an inclination of the ball hitting portion of the exercise appliance at impact.

Application Example 4

In the swing diagnosis apparatus according to the application example, the inclination of the ball hitting portion may be an angle formed between an outer edge of a hitting surface of the ball hitting portion and a virtual straight line orthogonal to a target hit ball direction in a plan view.

The inclination of the ball hitting portion may be an angle formed between a line of intersection of a hitting surface of the ball hitting portion and a reference plane (for example, a horizontal plane), and a virtual straight line orthogonal to a target hit ball direction in the reference plane.

According to the swing diagnosis apparatus of this application example, it is possible to grade and clearly show a feature of the swing based on a relationship between a rotation angle about the longitudinal direction of the exercise appliance at a desired timing during the swing and an inclination of the hitting surface of the exercise appliance at impact with respect to the target hit ball direction.

Application Example 5

In the swing diagnosis apparatus according to the application example, the level calculation section may calculate a lower level as a hit ball predicted on the basis of the relationship is more easily curved.

The term "easily curved" may indicate that a trajectory after ball hitting is easily curved, and may indicate that a hit ball direction is easily deviated relative to a target direction. The level calculation section may calculate a higher level as a hit ball more easily flies straight. The term "easily flies straight" may indicate that a trajectory after ball hitting is hardly curved, and may indicate that a hit ball direction is hardly deviated relative to a target direction.

According to the swing diagnosis apparatus of this application example, it is possible to grade and clearly show a feature of the swing till the impact according to the extent to which a hit ball is easily curved.

Application Example 6

In the swing diagnosis apparatus according to the application example, the level calculation section may calculate the level on the basis of a speed of the ball hitting portion at impact.

The level calculation section may calculate a level on the basis of a speed of the ball hitting portion at impact separately from the level calculated on the basis of the relationship. Alternatively, the level calculation section may calculate a single level (total score) on the basis of the relationship and the speed of the ball hitting portion at impact.

According to the swing diagnosis apparatus of this application example, it is possible to grade and clearly show a feature of the swing based on a speed of the ball hitting portion of the exercise appliance at impact.

Application Example 7

In the swing diagnosis apparatus according to the application example, the level calculation section may calculate a lower level as the speed becomes lower.

The level calculation section may calculate a higher level as the speed becomes higher.

According to the swing diagnosis apparatus of this application example, it is possible to grade and clearly show a feature of the swing according to a speed of the ball hitting portion at impact.

Application Example 8

The swing diagnosis apparatus according to the application example may further include a display section that displays the level calculated by the level calculation section.

According to the swing diagnosis apparatus of this application example, it is possible to present information obtained by leveling features of the swing till the impact so that the information can be easily visually recognized.

Application Example 9

In the swing diagnosis apparatus according to the application example, the level may be a score.

According to the swing diagnosis apparatus of this application example, it is possible to digitalize and clearly show features of the swing till the impact.

Application Example 10

A swing diagnosis system according to this application example includes any one of the swing diagnosis apparatuses according to the application examples; and an inertial sensor, in which the level calculation section calculates a level on the basis of outputs from the inertial sensor.

The inertial sensor may be a sensor which can measure an inertial amount such as acceleration or angular velocity, and may be, for example, an inertial measurement unit (IMU) which can measure acceleration or angular velocity. For example, the inertial sensor may be attached to an exercise appliance or a part of a user so as to be attachable to and detachable from the exercise appliance or the user, and may be fixed to the exercise appliance so as to not be detached therefrom as a result of being built into the exercise appliance.

According to the swing diagnosis system of this application example, the swing diagnosis apparatus calculates a level on the basis of a relationship between a rotation angle about a longitudinal direction of an exercise appliance at a desired timing during a swing, and an inclination of a ball hitting portion of the exercise appliance at impact, by using outputs from the inertial sensor, and can thus level and clearly show features of the swing till the impact.

Application Example 11

A swing diagnosis method according to this application example includes a procedure of calculating a level on the basis of a relationship between a rotation angle about a rotation axis of an exercise appliance at a predetermined timing between the time of starting a backswing and the time of impact with a longitudinal direction of the exercise appliance as the rotation axis, and an inclination of a ball hitting portion of the exercise appliance at impact.

Application Example 12

A swing diagnosis program according to this application example causes a computer to execute a procedure of calculating a level on the basis of a relationship between a rotation angle about a rotation axis of an exercise appliance at a predetermined timing between the time of starting a backswing and the time of impact with a longitudinal direction of the exercise appliance as the rotation axis, and an inclination of a ball hitting portion of the exercise appliance at impact.

Application Example 13

A recording medium according to this application example records a swing diagnosis program causing a computer to execute a procedure of calculating a level on the basis of a relationship between a rotation angle about a rotation axis of an exercise appliance at a predetermined timing between the time of starting a backswing and the time of impact with a longitudinal direction of the exercise appliance as the rotation axis, and an inclination of a ball hitting portion of the exercise appliance at impact.

According to the swing diagnosis method, the swing diagnosis program, and the recording medium of the application examples, since a level is calculated on the basis of a relationship between a rotation angle about a longitudinal direction of an exercise appliance at a desired timing during a swing, and an inclination of a ball hitting portion of the exercise appliance at impact, it is possible to grade and clearly show features of the swing till the impact.

BRIEF DESCRIPTION OF THE DRAWINGS

The invention will be described with reference to the accompanying drawings, wherein like numbers reference like elements.

FIG. 3 is a diagram illustrating procedures of actions performed by a user until the user hits a ball.

FIG. 4 is a diagram illustrating an example of an input screen of physical information and golf club information.

FIG. 6 is a diagram illustrating an example of a swing diagnosis screen.

FIG. 14A is a diagram illustrating an example of a rotation score table, and FIG. 14B is a diagram illustrating an example of a table defining a tendency of an impact zone.

FIG. 15 is a diagram illustrating an example of a speed score table.

DESCRIPTION OF EXEMPLARY EMBODIMENTS

Hereinafter, preferred embodiments of the invention will be described with reference to the drawings. The embodiments described below are not intended to improperly limit the content of the invention disclosed in the appended claims. In addition, all constituent elements described below are not essential constituent elements of the invention.

Hereinafter, a swing diagnosis system performing diagnosis of a golf swing will be described as an example.

1. Swing Diagnosis System

1-1. First Embodiment

1-1-1. Summary of Swing Diagnosis System

Figure 1:
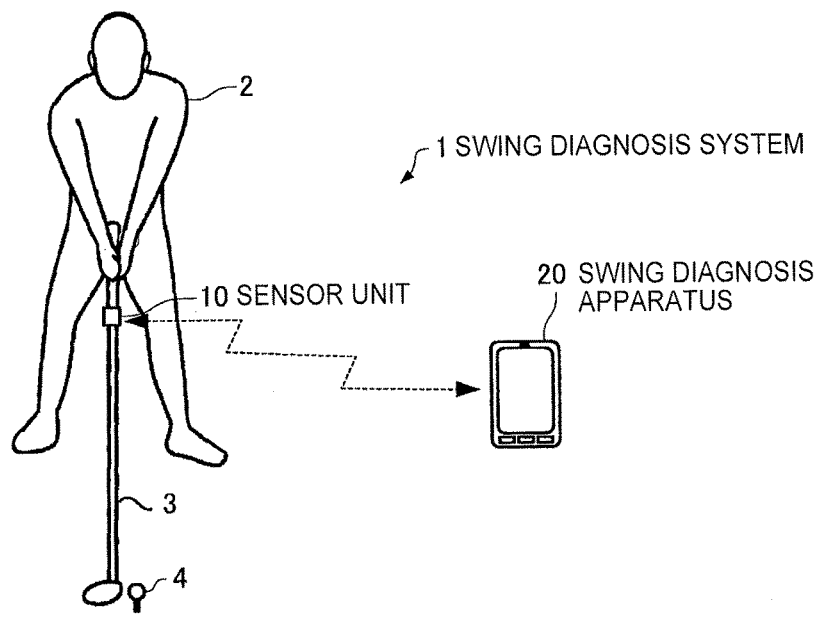
FIG. 1 is a diagram illustrating a summary of a swing diagnosis system of a first embodiment.

FIG. 1 is a diagram illustrating a summary of a swing diagnosis system of a first embodiment. A swing diagnosis system 1 of the first embodiment is configured to include a sensor unit 10 and a swing diagnosis apparatus 20.

Figure 2:
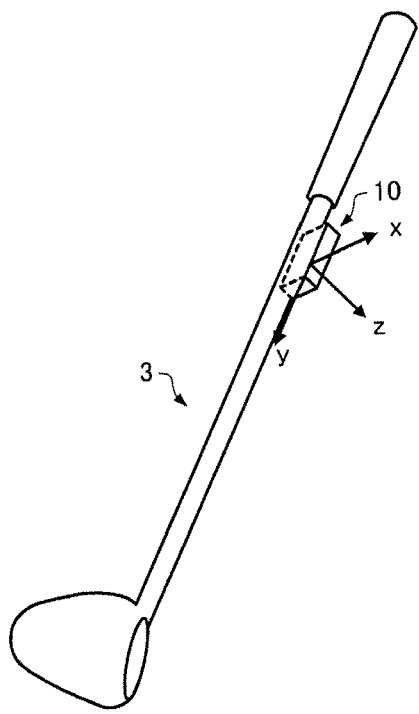
FIG. 2 is a diagram illustrating examples of a position at which and a direction in which the sensor unit is attached.

The sensor unit 10 (an example of an inertial sensor) can measure acceleration generated in each axial direction of three axes and angular velocity generated around each of the three axes, and is attached to a golf club 3 as illustrated in FIG. 2.

In the present embodiment, as illustrated in FIG. 2, the sensor unit 10 is attached to a part of a shaft so that one axis of three detection axes (an x axis, a y axis, and a z axis), for example, the y axis matches a longitudinal direction of the shaft of the golf club 3 (a longitudinal direction of the golf club 3). Preferably, the sensor unit 10 is attached to a position close to a grip to which impact during ball hitting is hardly forwarded and a centrifugal force is hardly applied during a swing. The shaft is a shaft portion other than a head of the golf club 3 and also includes the grip. However, the sensor unit 10 may be attached to a part (for example, the hand or a glove) of a user 2, and may be attached to an accessory such as a wristwatch.

The user 2 performs a swing action for hitting a golf ball 4 according to predefined procedures. FIG. 3 is a diagram illustrating procedures of actions performed by the user 2 until the user hits the ball. As illustrated in FIG. 3, first, the user 2 performs an input operation of physical information of the user 2, information (golf club information) regarding the golf club 3 used by the user 2, and the like via the swing diagnosis apparatus 20 (step S1). The physical information includes at least one of information regarding a height, a length of the arm, and a length of the legs of the user 2, and may further include information regarding sex or other information. The golf club information includes at least one of information regarding a length (club length) of the golf club 3 and the type (number) of golf club 3. Next, the user 2 performs a measurement starting operation (an operation for starting measurement in the sensor unit 10) via the swing diagnosis apparatus 20 (step S2). Next, after receiving a notification (for example, a notification using a voice) of giving an instruction for taking an address attitude (a basic attitude before starting a swing) from the swing diagnosis apparatus 20 (Y in step S3), the user 2 takes an address attitude so that the axis in the longitudinal direction of the shaft of the golf club 3 is perpendicular to a target line (target hit ball direction), and stands still (step S4). Next, the user 2 receives a notification (for example, a notification using a voice) of permitting a swing from the swing diagnosis apparatus 20 (Y in step S5), and then hits the golf ball 4 by performing a swing action (step S6).

FIG. 4 is a diagram illustrating an example of an input screen of physical information and golf club information, displayed on a display section 25 (refer to FIG. 7) of the swing diagnosis apparatus 20. In step S1 in FIG. 3, the user 2 inputs physical information such as a height, sex, age, and country, and inputs golf club information such as a club length, and a number on the input screen illustrated in FIG. 4. Information included in the physical information is not limited thereto, and, the physical information may include, for example, at least one of information regarding a length of the arms and a length of the legs instead of or along with the height. Similarly, information included in the golf club information is not limited thereto, and, for example, the golf club information may not include at least one of information regarding the club length and the number, and may include other information.

If the user 2 performs the measurement starting operation in step S2 in FIG. 3, the swing diagnosis apparatus 20 transmits a measurement starting command to the sensor unit 10, and the sensor unit 10 receives the measurement starting command and starts measurement of three-axis accelerations and three-axis angular velocities. The sensor unit 10 measures three-axis accelerations and three-axis angular velocities in a predetermined cycle (for example, 1 ms), and sequentially transmits the measured data to the swing diagnosis apparatus 20. Communication between the sensor unit 10 and the swing diagnosis apparatus 20 may be wireless communication, and may be wired communication.

The swing diagnosis apparatus 20 notifies the user 2 of permission of swing starting, shown in step S5 in FIG. 3, and then analyzes the swing action (step S6 in FIG. 3) in which the user 2 has hit the ball by using the golf club 3 on the basis of measured data (an example of an output from an inertial sensor) from the sensor unit 10.

Figure 5:
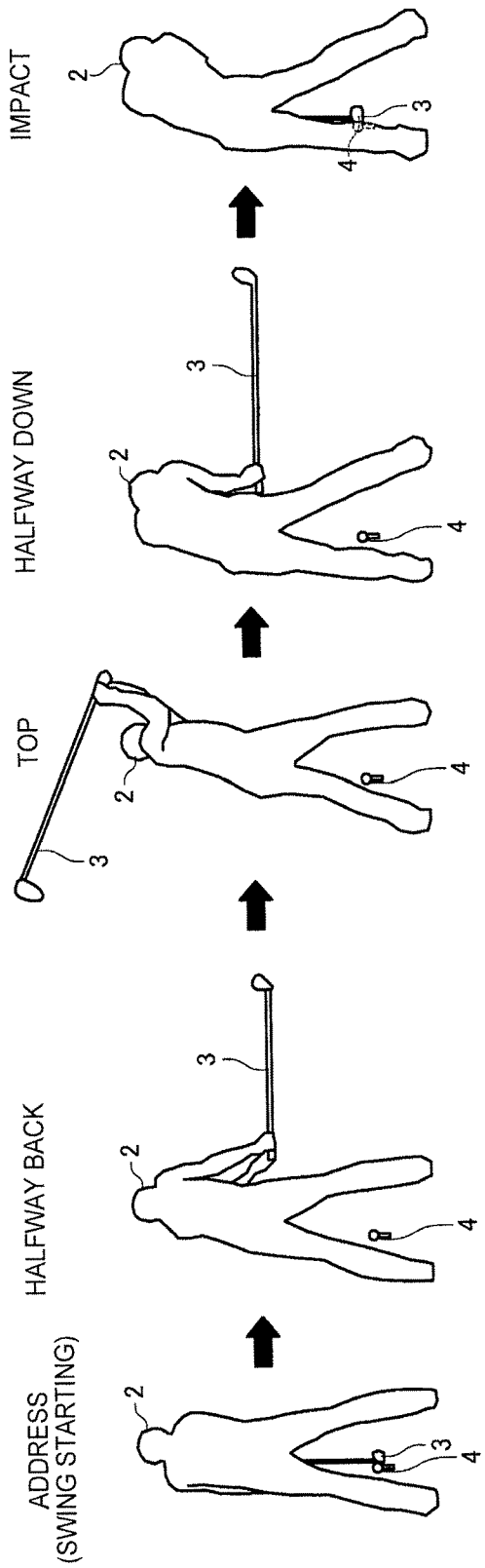
FIG. 5 is a diagram illustrating a swing action.

As illustrated in FIG. 5, the swing action performed by the user 2 in step S6 in FIG. 3 includes an action reaching impact (ball hitting) at which the golf ball 4 is hit through respective states of halfway back at which the shaft of the golf club 3 becomes horizontal during a backswing after starting a swing (backswing), a top at which the swing changes from the backswing to a downswing, and halfway down at which the shaft of the golf club 3 becomes horizontal during the downswing. The swing diagnosis apparatus 20 generates swing analysis data including information regarding a time point (date and time) at which the swing is performed, identification information or the sex of the user 2, the type of golf club 3, and an analysis result of the swing action.

The swing diagnosis apparatus 20 calculates levels of predetermined items indicating features of a swing of the user 2 by using the swing analysis data generated on the basis of the measured data in the sensor unit 10. Specifically, the swing diagnosis apparatus 20 calculates levels of respective two items such as a "rotation" item and a "speed" item (for example, 5 points maximum). Meanings or a calculation method of the two items will be described later. The swing diagnosis apparatus 20 may calculate a total score of the swing by using the levels of the two items. The "levels" may be represented by, for example, "1, 2, 3, . . . ", "A, B, C, . . . ", "○, X, Δ", and may be represented by scores.

The swing diagnosis apparatus 20 displays, for example, a swing diagnosis screen as illustrated in FIG. 6 on the display section 25 by using information regarding the calculated levels and total score of the predetermined items. The swing diagnosis screen illustrated in FIG. 6 includes information regarding the swing analysis data on a left part thereof. The information regarding the swing analysis data is data information used for diagnosis of the swing (that is, calculation of the levels and the total score of the two items) in the swing diagnosis apparatus 20. The information regarding the swing analysis data includes values obtained on the basis of the swing analysis data with respect to the sex, the type of golf club (a driver or an iron), and respective indexes of the swing. Meanings or a calculation method of the respective indexes (a face angle, a shaft axis rotation angle at top, and a head speed) will be described later. The swing diagnosis screen illustrated in FIG. 6 includes information regarding scores as the levels of the two items and the total score on a right part thereof.

The user 2 can understand levels and a total score of predetermined items as diagnosis results for the swing analysis data on the left part on the basis of the swing diagnosis screen illustrated in FIG. 6. Particularly, if the user 2 can understand strong points or weak points in the user's swing on the basis of the swing diagnosis screen illustrated in FIG. 6. Hereinafter, a description will be made of an example in which "levels" of predetermined items are represented by "scores", but, needless to say, the example can be easily replaced with an example of the levels being expressed by "1, 2, 3, . . . ", "A, B, C, . . . ", "○, X, Δ", or the like.

For example, the swing diagnosis apparatus 20 may be implemented by an information terminal (client terminal) such as a smart phone or a personal computer.

1-1-2. Configuration of Sensor Unit and Swing Diagnosis Apparatus

Figure 7:
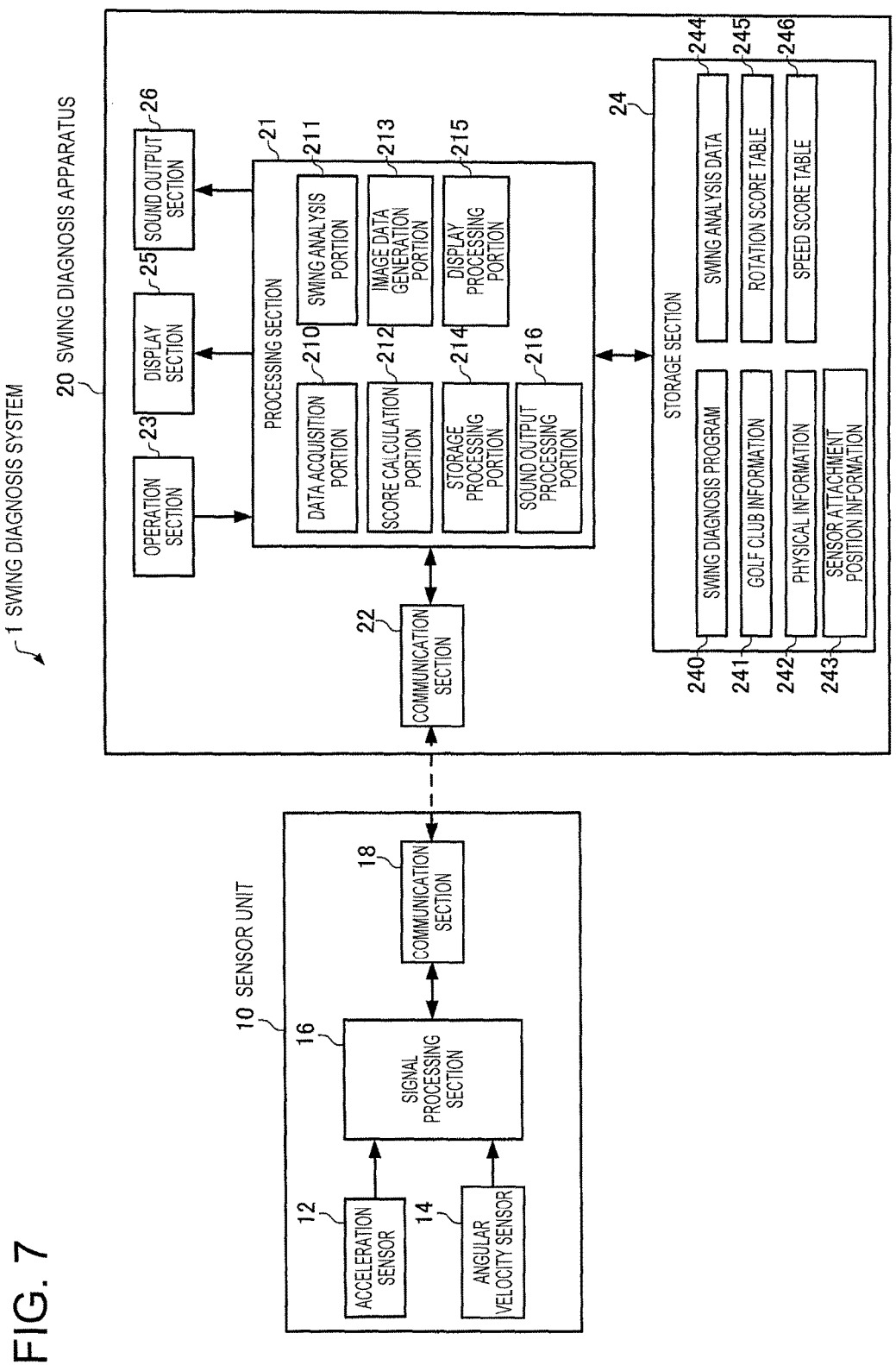
FIG. 7 is a diagram illustrating a configuration example of a swing diagnosis system of the first embodiment.

FIG. 7 is a diagram illustrating configuration examples (configuration examples of the sensor unit 10 and the swing diagnosis apparatus 20) of the swing diagnosis system 1 of the first embodiment. As illustrated in FIG. 7, in the present embodiment, the sensor unit 10 is configured to include an acceleration sensor 12, an angular velocity sensor 14, a signal processing section 16, and a communication section 18. However, the sensor unit 10 may have a configuration in which some of the constituent elements are deleted or changed as appropriate, or may have a configuration in which other constituent elements are added thereto.

The acceleration sensor 12 measures respective accelerations generated in three axial directions which intersect (ideally, orthogonal to) each other, and outputs digital signals (acceleration data) corresponding to magnitudes and directions of the measured three-axis accelerations.

The angular velocity sensor 14 measures respective angular velocities generated around each of the three axes which intersect (ideally, orthogonal to) each other, and outputs digital signals (angular velocity data) corresponding to magnitudes and directions of the measured three-axis angular velocities.

The signal processing section 16 receives the acceleration data and the angular velocity data from the acceleration sensor 12 and the angular velocity sensor 14, respectively, adds time information thereto, stores the data in a storage portion (not illustrated), adds time information to the stored measured data (acceleration data and angular velocity data) so as to generate packet data conforming to a communication format, and outputs the packet data to the communication section 18.

Ideally, the acceleration sensor 12 and the angular velocity sensor 14 are provided in the sensor unit 10 so that the three axes thereof match three axes (an x axis, a y axis, and a z axis) of an orthogonal coordinate system (sensor coordinate system) defined for the sensor unit 10, but, actually, errors occur in installation angles. Therefore, the signal processing section 16 performs a process of converting the acceleration data and the angular velocity data into data in the xyz coordinate system by using a correction parameter which is calculated in advance according to the installation angle errors.

The signal processing section 16 may perform a process of correcting the temperatures of the acceleration sensor 12 and the angular velocity sensor 14. The acceleration sensor 12 and the angular velocity sensor 14 may have a temperature correction function.

The acceleration sensor 12 and the angular velocity sensor 14 may output analog signals, and, in this case, the signal processing section 16 may A/D convert an output signal from the acceleration sensor 12 and an output signal from the angular velocity sensor 14 so as to generate measured data (acceleration data and angular velocity data), and may generate communication packet data by using the data.

The communication section 18 performs a process of transmitting packet data received from the signal processing section 16 to the swing diagnosis apparatus 20, or a process of receiving various control commands, such as a measurement starting command, from the swing diagnosis apparatus 20 and sending the control command to the signal processing section 16. The signal processing section 16 performs various processes corresponding to control commands.

As illustrated in FIG. 7, in the present embodiment, the swing diagnosis apparatus 20 is configured to include a processing section 21, a communication section 22, an operation section 23, a storage section 24, the display section 25, and a sound output section 26. However, the swing diagnosis apparatus 20 may have a configuration in which some of the constituent elements are deleted or changed as appropriate, or may have a configuration in which other constituent elements are added thereto.

The communication section 22 performs a process of receiving packet data transmitted from the sensor unit 10 and sending the packet data to the processing section 21, or a process of transmitting a control command from the processing section 21 to the sensor unit 10.

The operation section 23 performs a process of acquiring operation data from the user 2 and sending the operation data to the processing section 21. The operation section 23 may be, for example, a touch panel type display, a button, a key, or a microphone.

The storage section 24 is constituted of, for example, various IC memories such as a read only memory (ROM), a flash ROM, and a random access memory (RAM), or a recording medium such as a hard disk or a memory card. The storage section 24 stores a program for the processing section 21 performing various calculation processes or a control process, or various programs or data for realizing application functions.

In the present embodiment, the storage section 24 stores a swing diagnosis program 240 which is read by the processing section 21 and executes a swing diagnosis process. The swing diagnosis program 240 may be stored in a nonvolatile recording medium (computer readable recording medium) in advance, or the swing diagnosis program 240 may be received from a server (not illustrated) by the processing section 21 via a network, and may be stored in the storage section 24.

In the present embodiment, the storage section 24 stores golf club information 241, physical information 242, sensor attachment position information 243, and swing analysis data 244. For example, the user 2 may operate the operation section 23 so as to input specification information regarding the golf club 3 to use (for example, at least some information such as information regarding a length of the shaft, a position of the centroid thereof, a lie angle, a face angle, a loft angle, and the like) from the input screen illustrated in FIG. 4, and the input specification information may be used as the golf club information 241. Alternatively, in step S1 in FIG. 3, the user 2 may sequentially input type numbers of the golf club 3 (alternatively, selects a type number from a type number list) so that specification information for each type number is stored in the storage section 24 in advance. In this case, specification information of an input type number may be used as the golf club information 241.

For example, the user 2 may input physical information by operating the operation section 23 from the input screen illustrated in FIG. 4, and the input physical information may be used as the physical information 242. For example, in step S1 in FIG. 3, the user 2 may input a distance between an attachment position of the sensor unit 10 and the grip end of the golf club 3 by operating the operation section 23, and the input distance information may be used as the sensor attachment position information 243. Alternatively, the sensor unit 10 may be attached at a defined predetermined position (for example, a distance of 20 cm from the grip end), and thus information regarding the predetermined position may be stored as the sensor attachment position information 243 in advance.

The swing analysis data 244 is data including information regarding a swing action analysis result in the processing section 21 (swing analysis portion 211) along with a time point (date and time) at which a swing was performed, identification information or the sex of the user 2, and the type of golf club 3.

The storage section 24 stores a rotation score table 245 and a speed score table 246. The score tables will be described later in detail.

The storage section 24 is used as a work area of the processing section 21, and temporarily stores data which is input from the operation section 23, results of calculation executed by the processing section 21 according to various programs, and the like. The storage section 24 may store data which is required to be preserved for a long period of time among data items generated through processing of the processing section 21.

The display section 25 displays a processing result in the processing section 21 as text, a graph, a table, animation, and other images. The display section 25 may be, for example, a CRT, an LCD, a touch panel type display, and a head mounted display (HMD). A single touch panel type display may realize functions of the operation section 23 and the display section 25.

The sound output section 26 outputs a processing result in the processing section 21 as a sound such as a voice or a buzzer sound. The sound output section 26 may be, for example, a speaker or a buzzer.

The processing section 21 performs a process of transmitting a control command to the sensor unit 10 via the communication section 22, or various computation processes on data which is received from the sensor unit 10 via the communication section 22, according to various programs. The processing section 21 performs a process of reading the swing analysis data 244 from the storage section 24, so as to calculate scores or a total score of predetermined items and to display the swing diagnosis screen (FIG. 6), according to various programs. The processing section 21 performs other various control processes.

Particularly, in the present embodiment, by executing the swing diagnosis program 240, the processing section 21 functions as a data acquisition portion 210, a swing analysis portion 211, a score calculation portion 212, an image data generation portion 213, a storage processing portion 214, a display processing portion 215, and a sound output processing portion 216, and performs a process (swing diagnosis process) of diagnosing a swing action of the user 2. In the present embodiment, the swing diagnosis process includes a process (swing analysis process) of analyzing the swing action of the user 2 and a process (score calculation process) of calculating a score of the swing action.

The data acquisition portion 210 performs a process of receiving packet data which is received from the sensor unit 10 by the communication section 22, acquiring time information and measured data in the sensor unit 10 from the received packet data, and sending the time information and the measured data to the storage processing portion 214.

The storage processing portion 214 performs read/write processes of various programs or various data for the storage section 24. The storage processing portion 214 performs not only the process of storing the time information and the measured data received from the data acquisition portion 210 in the storage section 24 in correlation with each other, but also a process of storing various pieces of information calculated by the swing analysis portion 211, the swing analysis data 244, or the like in the storage section 24. For example, the storage processing portion 214 performs a process of reading the swing analysis data 244, the rotation score table 245, and the speed score table 246 stored in the storage section 24, and transmitting the data and the tables to the score calculation portion 212.

The swing analysis portion 211 performs a process of analyzing a swing action of the user 2 by using the measured data (the measured data stored in the storage section 24) output from the sensor unit 10, the data from the operation section 23, or the like, so as to generate the swing analysis data 244 including a time point (date and time) at which the swing was performed, identification information or the sex of the user 2, the type of golf club 3, and information regarding a swing action analysis result. Particularly, in the present embodiment, the swing analysis portion 211 calculates a value of each index of the swing as at least some of the information regarding the swing action analysis result.

The swing analysis portion 211 may calculate an index based on an inclination of the head of the golf club 3 at impact (at ball hitting) as an index of the swing. For example, the swing analysis portion 211 may calculate a "face angle $\phi$" which will be described later as the index.

The swing analysis portion 211 may calculate an index based on a rotation angle about a rotation axis (hereinafter, referred to as about the long axis) of the shaft of the golf club 3 at a predetermined timing between the time of starting a backswing and the time of impact (at ball hitting) with a longitudinal direction of the shaft as the rotation axis, as an index of the swing. The rotation angle about the long axis of the golf club 3 may be an angle by which the golf club 3 is rotated about the long axis from a reference timing to a predetermined timing. The reference timing may be the time of starting a backswing, and may be the time of address. The predetermined timing may be the time (the time of a top) at which a backswing transitions to a downswing. For example, the swing analysis portion 211 may calculate a "shaft axis rotation angle $\theta_{top}$ at top" which will be described later as the index.

The swing analysis portion 211 may calculate an index based on a speed of the golf club 3 at impact (at ball hitting) as an index of the swing. For example, the swing analysis portion 211 may calculate a "head speed" which will be described later as the index.

However, the swing analysis portion 211 may not calculate values of some of the indexes, and may calculate values of other indexes, as appropriate.

The score calculation portion 212 (level calculation section) performs a process of calculating scores (levels) of predetermined items indicating features of the swing of the user 2 on the basis of data regarding the swing. In the present embodiment, the data regarding the swing is the swing analysis data 244.

The score calculation portion 212 performs a process of calculating a total score on the basis of the scores of the predetermined items. The score calculation portion 212 performs a process of transmitting information regarding the calculated scores and total score of the predetermined items to the image data generation portion 213.

The image data generation portion 213 performs a process of generating image data corresponding to an image displayed on the display section 25. For example, the image data generation portion 213 generates image data corresponding to the swing diagnosis screen illustrated in FIG. 6 on the basis of the information regarding the calculated scores and total score of the predetermined items received from the score calculation portion 212.

The display processing portion 215 performs a process of displaying various images (including text, symbols, and the like in addition to an image corresponding to the image data generated by the image data generation portion 213) on the display section 25. For example, the display processing portion 215 displays the swing diagnosis screen illustrated in FIG. 6, and the like, on the display section 25, on the basis of the image data generated by the image data generation portion 213. For example, the image data generation portion 213 may display an image, text, or the like for notifying the user 2 of permission of swing starting on the display section 25 in step S5 in FIG. 3. For example, the display processing portion 215 may display text information such as text or symbols indicating an analysis result in the swing analysis portion 211 on the display section 25 automatically or in response to an input operation performed by the user 2 after a swing action of the user 2 is completed. Alternatively, a display section may be provided in the sensor unit 10, and the display processing portion 215 may transmit image data to the sensor unit 10 via the communication section 22, and various images, text, or the like may be displayed on the display section of the sensor unit 10.

The sound output processing portion 216 performs a process of outputting various sounds (including voices, buzzer sounds, and the like) from the sound output section 26. For example, the sound output processing portion 216 may output a sound for notifying the user 2 of permission of swing starting from the sound output section 26 in step S5 in FIG. 3. For example, the sound output processing portion 216 may output a sound or a voice indicating an analysis result in the swing analysis portion 211 from the sound output section 26 automatically or in response to an input operation performed by the user 2 after a swing action of the user 2 is completed. Alternatively, a sound output section may be provided in the sensor unit 10, and the sound output processing portion 216 may transmit various items of sound data or voice data to the sensor unit 10 via the communication section 22, and may output various sounds or voices from the sound output section of the sensor unit 10.

A vibration mechanism may be provided in the swing diagnosis apparatus 20 or the sensor unit 10, and various pieces of information may be converted into vibration pieces of information by the vibration mechanism so as to be presented to the user 2.

1-1-3. Swing Analysis Process

In the present embodiment, when a position of the head of the golf club 3 at address (during standing still) is set to the origin, an XYZ coordinate system (global coordinate system) is defined which has a target line indicating a target hit ball direction as an X axis, an axis on a horizontal plane which is perpendicular to the X axis as a Y axis, and a vertically upward direction (a direction opposite to the gravitational acceleration direction) as a Z axis. In order to calculate each index value, the swing analysis portion 211 calculates a position and an attitude of the sensor unit 10 in a time series from the time of the address in the XYZ coordinate system (global coordinate system) by using measured data (acceleration data and angular velocity data) in the sensor unit 10. The swing analysis portion 211 detects respective timings of the swing starting, the top, and the impact illustrated in FIG. 5, by using the measured data (acceleration data or angular velocity data) in the sensor unit 10. The swing analysis portion 211 calculates values of the respective indexes (for example, a face angle $\phi$, a shaft axis rotation angle $\theta_{top}$ at top, and a head speed) of the swing by using the time series data of the position and the attitude of the sensor unit 10, and the timings of the swing starting, the top, and the impact, so as to generate the swing analysis data 244.

Calculation of Position and Attitude of Sensor Unit 10

If the user 2 performs the action in step S4 in FIG. 3, first, the swing analysis portion 211 determines that the user 2 stands still at an address attitude in a case where an amount of changes in acceleration data measured by the acceleration sensor 12 does not continuously exceed a threshold value for a predetermined period of time. Next, the swing analysis portion 211 computes an offset amount included in the measured data by using the measured data (acceleration data and angular velocity data) for the predetermined period of time. Next, the swing analysis portion 211 subtracts the offset amount from the measured data so as to perform bias correction, and computes a position and an attitude of the sensor unit 10 during a swing action of the user 2 (during the action in step S6 in FIG. 3) by using the bias-corrected measured data.

Specifically, first, the swing analysis portion 211 computes a position (initial position) of the sensor unit 10 during standing still (at address) of the user 2 in the XYZ coordinate system (global coordinate system) by using the acceleration data measured by the acceleration sensor 12, the golf club information 241, and the sensor attachment position information 243.

Figure 8:
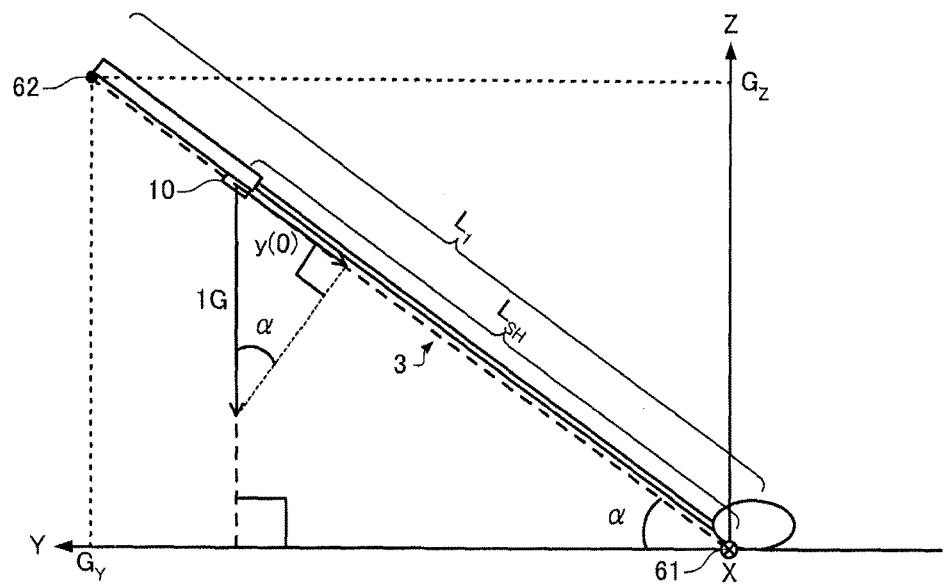
FIG. 8 is a plan view in which a golf club and the sensor unit are viewed from a negative side of an X axis during standing still of the user.

FIG. 8 is a plan view in which the golf club 3 and the sensor unit 10 during standing still (at address) of the user 2 are viewed from a negative side of the X axis. The origin O (0,0,0) is set at a position 61 of the head of the golf club 3, and coordinates of a position 62 of a grip end are (0, $G_Y$, $G_Z$). Since the user 2 performs the action in step S4 in FIG. 3, the position 62 of the grip end or the initial position of the sensor unit 10 has an X coordinate of 0, and is present on a YZ plane. As illustrated in FIG. 8, the gravitational acceleration of 1 G is applied to the sensor unit 10 during standing still of the user 2, and thus a relationship between a y axis acceleration y(0) measured by the sensor unit 10 and an inclined angle (an angle formed between the longitudinal direction of the shaft and the horizontal plane (XY plane)) $\alpha$ of the shaft of the golf club 3 is expressed by Equation (1).

$$y(0) = 1G \cdot \sin \alpha \qquad (1)$$

Therefore, the swing analysis portion 211 can calculate the inclined angle $\alpha$ according to Equation (1) by using any acceleration data between any time points at address (during standing still).

Next, the swing analysis portion 211 subtracts a distance $L_{SG}$ between the sensor unit 10 and the grip end included in the sensor attachment position information 243 from a length $L_1$ of the shaft included in the golf club information 241, so as to obtain a distance $L_{SH}$ between the sensor unit 10 and the head. The swing analysis portion 211 sets, as the initial position of the sensor unit 10, a position separated by the distance $L_{SH}$ from the position 61 (origin O) of the head in a direction (a negative direction of the y axis of the sensor unit 10) specified by the inclined angle $\alpha$ of the shaft.

The swing analysis portion 211 integrates subsequent acceleration data so as to compute coordinates of a position from the initial position of the sensor unit 10 in a time series.

The swing analysis portion 211 computes an attitude (initial attitude) of the sensor unit 10 during standing still (at address) of the user 2 in the XYZ coordinate system (global coordinate system) by using acceleration data measured by the acceleration sensor 12. Since the user 2 performs the action in step S4 in FIG. 3, the x axis of the sensor unit 10 matches the X axis of the XYZ coordinate system in terms of direction at address (during standing still) of the user 2, and the y axis of the sensor unit 10 is present on the YZ plane. Therefore, the swing analysis portion 211 can specify the initial attitude of the sensor unit 10 on the basis of the inclined angle $\alpha$ of the shaft of the golf club 3.

The swing analysis portion 211 computes changes in attitudes from the initial attitude of the sensor unit 10 in time series by performing rotation calculation using angular velocity data which is subsequently measured by the angular velocity sensor 14. An attitude of the sensor unit 10 may be expressed by, for example, rotation angles (a roll angle, a pitch angle, and a yaw angle) about the X axis, the Y axis, and the Z axis, or a quaternion.

The signal processing section 16 of the sensor unit 10 may compute an offset amount of measured data so as to perform bias correction on the measured data, and the acceleration sensor 12 and the angular velocity sensor 14 may have a bias correction function. In this case, it is not necessary for the swing analysis portion 211 to perform bias correction on the measured data.

Detection of Swing Starting, Top and Impact Timings

First, the swing analysis portion 211 detects a timing (impact timing) at which the user 2 hits a ball by using measured data. For example, the swing analysis portion 211 may compute a combined value of measured data (acceleration data or angular velocity data), and may detect an impact timing (time point) on the basis of the combined value.

Specifically, first, the swing analysis portion 211 computes a combined value $n_0(t)$ of angular velocities at each time point t by using the angular velocity data (bias-corrected angular velocity data for each time point t). For example, if the angular velocity data items at the time point t are respectively indicated by x(t), y(t), and z(t), the swing analysis portion 211 computes the combined value $n_0(t)$ of the angular velocities according to the following Equation (2).

$$n_0(t) = \sqrt{x(t)^2 + y(t)^2 + z(t)^2} \qquad (2)$$

Next, the swing analysis portion 211 converts the combined value $n_0(t)$ of the angular velocities at each time point t into a combined value n(t) which is normalized (scale-conversion) within a predetermined range. For example, if the maximum value of the combined value of the angular velocities in an acquisition period of measured data is max($n_0$), the swing analysis portion 211 converts the combined value $n_0(t)$ of the angular velocities into the combined value n(t) which is normalized within a range of 0 to 100 according to the following Equation (3).

$$n(t) = \frac{100 \times n_0(t)}{\max(n_0)} \quad (3)$$

Next, the swing analysis portion 211 computes a derivative dn(t) of the normalized combined value n(t) at each time point t. For example, if a cycle for measuring three-axis angular velocity data items is indicated by Δt, the swing analysis portion 211 computes the derivative (difference) dn(t) of the combined value of the angular velocities at the time point t by using the following Equation (4).

$$dn(t) = n(t) - n(t - \Delta t) \quad (4)$$

Figure 9:
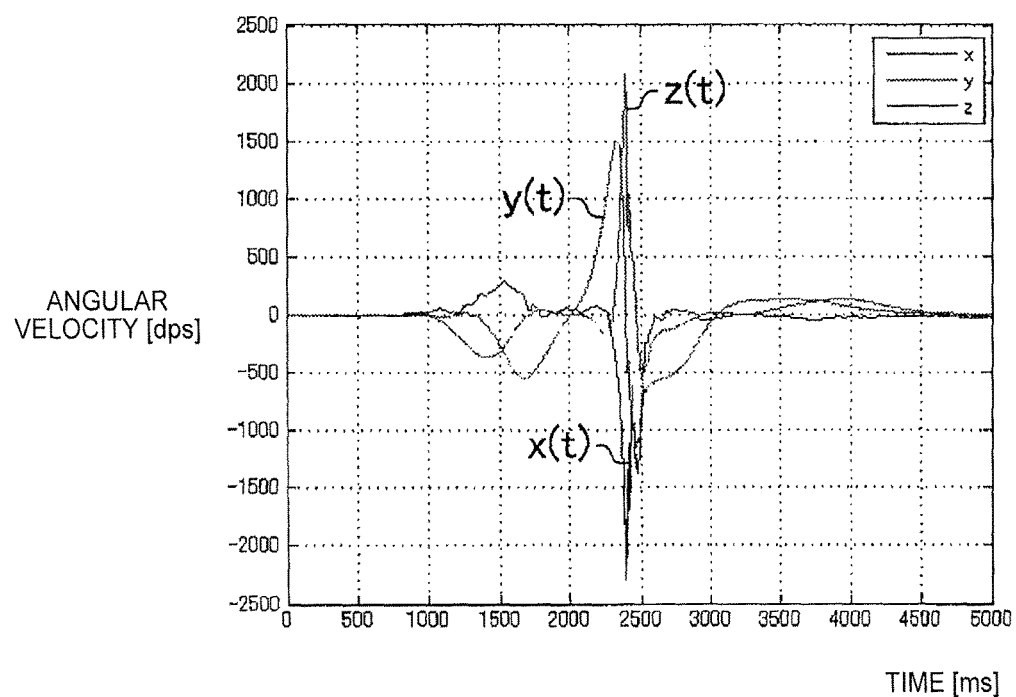
FIG. 9 is a graph illustrating examples of temporal changes of three-axis angular velocities.

FIG. 9 illustrates examples of three-axis angular velocity data items x(t), y(t) and z(t) obtained when the user 2 hits the golf ball 4 by performing a swing. In FIG. 9, a transverse axis expresses time (msec), and a longitudinal axis expresses angular velocity (dps).

Figure 10:
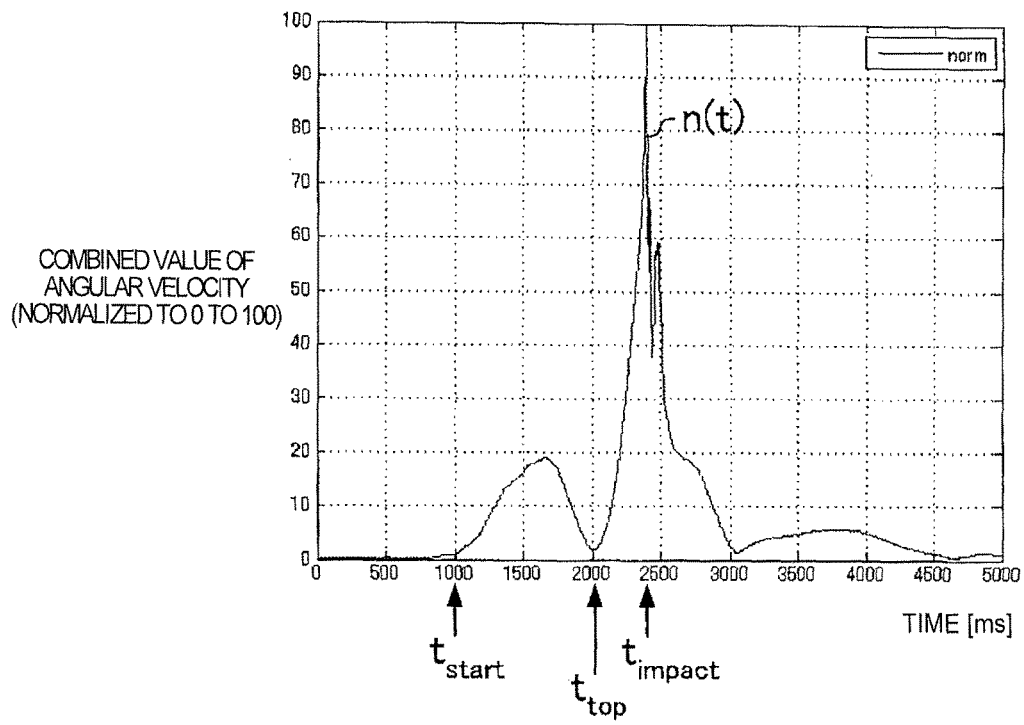
FIG. 10 is a graph illustrating a temporal change of a combined value of the three-axis angular velocities.

FIG. 10 is a diagram in which the combined value $n_0(t)$ of the three-axis angular velocities is computed according to Equation (2) by using the three-axis angular velocity data items x(t), y(t) and z(t) in FIG. 9, and then the combined value n(t) normalized to 0 to 100 according to Equation (3) is displayed in a graph. In FIG. 10, a transverse axis expresses time (msec), and a longitudinal axis expresses a combined value of the angular velocity.

Figure 11:
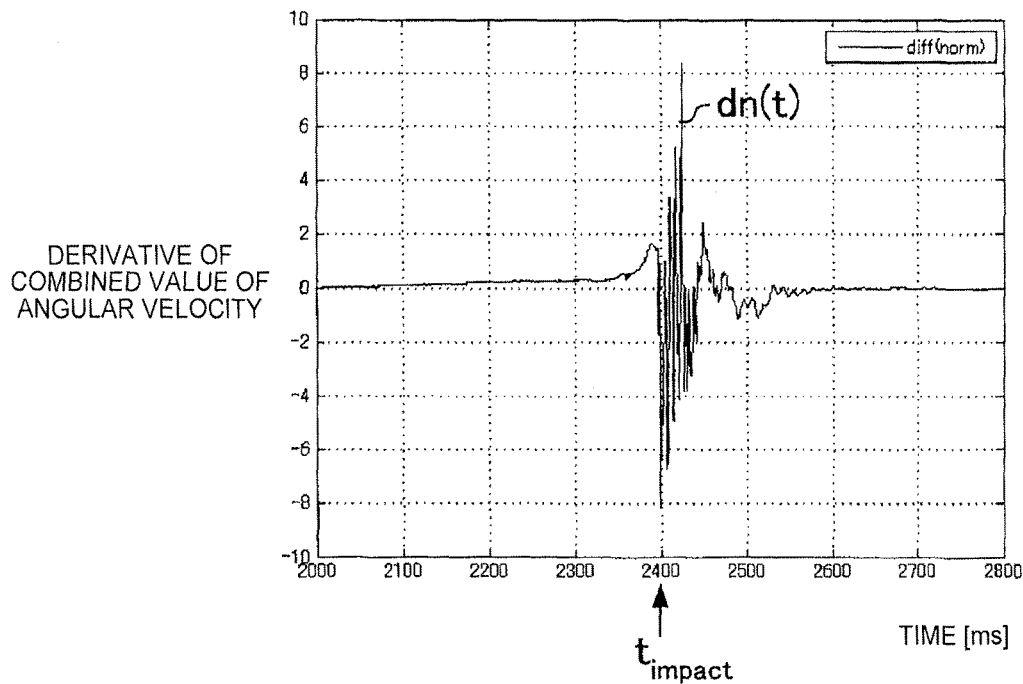
FIG. 11 is a graph illustrating a temporal change of a derivative of the combined value.

FIG. 11 is a diagram in which the derivative dn(t) is calculated according to Equation (4) on the basis of the combined value n(t) of the three-axis angular velocities in FIG. 10, and is displayed in a graph. In FIG. 11, a transverse axis expresses time (msec), and a longitudinal axis expresses a derivative value of the combined value of the three-axis angular velocities. In FIGS. 9 and 10, the transverse axis is displayed at 0 seconds to 5 seconds, but, in FIG. 11, the transverse axis is displayed at 2 seconds to 2.8 seconds so that changes in the derivative value before and after impact can be understood.

Next, of time points at which a value of the derivative dn(t) of the combined value becomes the maximum and the minimum, the swing analysis portion 211 specifies the earlier time point as an impact time point $t_{impact}$ (impact timing) (refer to FIG. 11). It is considered that swing speed is the maximum at the moment of impact in a typical golf swing. In addition, since it is considered that a value of the combined value of the angular velocities also changes according to a swing speed, the swing analysis portion 211 can capture a timing at which a derivative value of the combined value of the angular velocities is the maximum or the minimum (that is, a timing at which the derivative value of the combined value of the angular velocities is a positive maximum value or a negative minimum value) in a series of swing actions as the impact timing. Since the golf club 3 vibrates due to the impact, a timing at which a derivative value of the combined value of the angular velocities is the maximum and a timing at which a derivative value of the combined value of the angular velocities is the minimum may occur in pairs, and, of the two timings, the earlier timing may be the moment of the impact.

Next, the swing analysis portion 211 specifies a time point of a minimum point at which the combined value n(t) is close to 0 before the impact time point $t_{impact}$, as a top time point $t_{top}$ (top timing) (refer to FIG. 10). It is considered that, in a typical golf swing, an action temporarily stops at the top after starting the swing, then a swing speed increases, and finally impact occurs. Therefore, the swing analysis portion 211 can capture a timing at which the combined value of the angular velocities is close to 0 and becomes the minimum before the impact timing, as the top timing.

Next, the swing analysis portion 211 sets an interval in which the combined value n(t) is equal to or smaller than a predetermined threshold value before and after the top time point $t_{top}$, as a top interval, and detects a last time point at which the combined value n(t) is equal to or smaller than the predetermined threshold value before a starting time point of the top interval, as a swing starting (backswing starting) time point $t_{start}$ (refer to FIG. 10). It is hardly considered that, in a typical golf swing, a swing action is started from a standing still state, and the swing action is stopped till the top. Therefore, the swing analysis portion 211 can capture the last timing at which the combined value of the angular velocities is equal to or smaller than the predetermined threshold value before the top interval as a timing of starting the swing action. The swing analysis portion 211 may detect a time point of the minimum point at which the combined value n(t) is close to 0 before the top time point $t_{top}$ as the swing starting time point $t_{start}$.

The swing analysis portion 211 may also detect each of a swing starting timing, a top timing, an impact timing by using three-axis acceleration data in the same manner.

Calculation of Face Angle

A face angle is an index based on an inclination of the head of the golf club 3 at impact.

Figure 12:
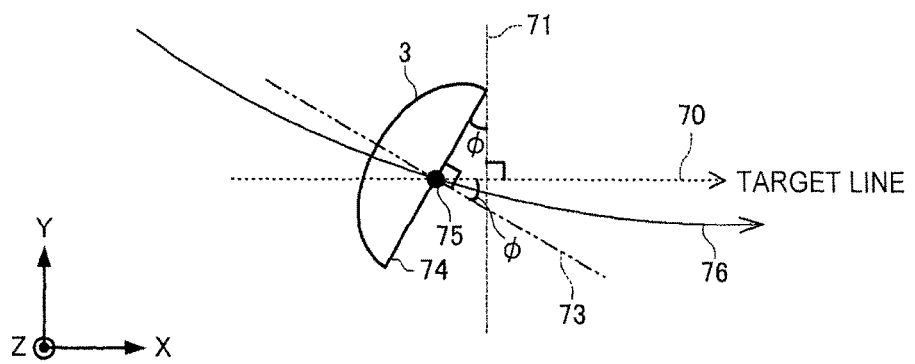
FIG. 12 is a diagram for explaining a face angle.

FIG. 12 is a diagram for explaining the face angle. FIG. 12 illustrates the golf club 3 (only the head is illustrated) on the XY plane viewed from a positive side of the Z axis (an upper side of the user 2) in the XYZ coordinate system. In FIG. 12, the reference numeral 74 indicates a face surface (hitting surface) of the head of the golf club 3, and the reference numeral 75 indicates a ball hitting point. The reference numeral 70 indicates a target line indicating a target hit ball direction, and the reference numeral 71 indicates a plane orthogonal to the target line 70. The reference numeral 76 indicates a curve indicating a trajectory of the head of the golf club 3. In this case, the face angle φ is an angle formed between an outer edge (an outer edge on the ground side) of the face surface 74 and a virtual line (a line of intersection of the plane 71 and the XY plane) orthogonal to the target line 70 in a plan view (on the XY plane), that is, an angle formed between the straight line 73 orthogonal to the outer edge (the outer edge on the ground side) of the face surface 74, and the target line 70.

For example, assuming that an angle formed between the face surface of the head and the x axis direction is normally constant (for example, orthogonal to each other), the swing analysis portion 211 computes a direction of a straight line orthogonal to the face surface on the basis of the attitude of the sensor unit 10 at the impact time point $t_{impact}$. The swing analysis portion 211 uses, a straight line obtained by setting a Z axis component of the direction of the straight line to 0, as a direction of the straight line 73, and computes an angle (face angle) φ formed between the straight line 73 and the target line 70.

Calculation of Shaft Axis Rotation Angle at Top

The shaft axis rotation angle $\theta_{top}$ at top is an angle (relative rotation angle) by which the golf club 3 is rotated about a rotation axis from a reference timing to a top timing. The reference timing is, for example, the time of starting a backswing, or the time of address. In the present embodiment, in a case where the user 2 is a right-handed golfer, a right-handed screw tightening direction toward the tip end on the head side of the golf club 3 (a clockwise direction when the head is viewed from the grip end side) is a positive direction of the shaft axis rotation angle $\theta_{top}$. Conversely, in a case where the user 2 is a left-handed golfer, a left-handed screw tightening direction toward the tip end on the head side of the golf club 3 (a counterclockwise direction when the head is viewed from the grip end side) is a positive direction of the shaft axis rotation angle $\theta_{top}$.

Figure 13:
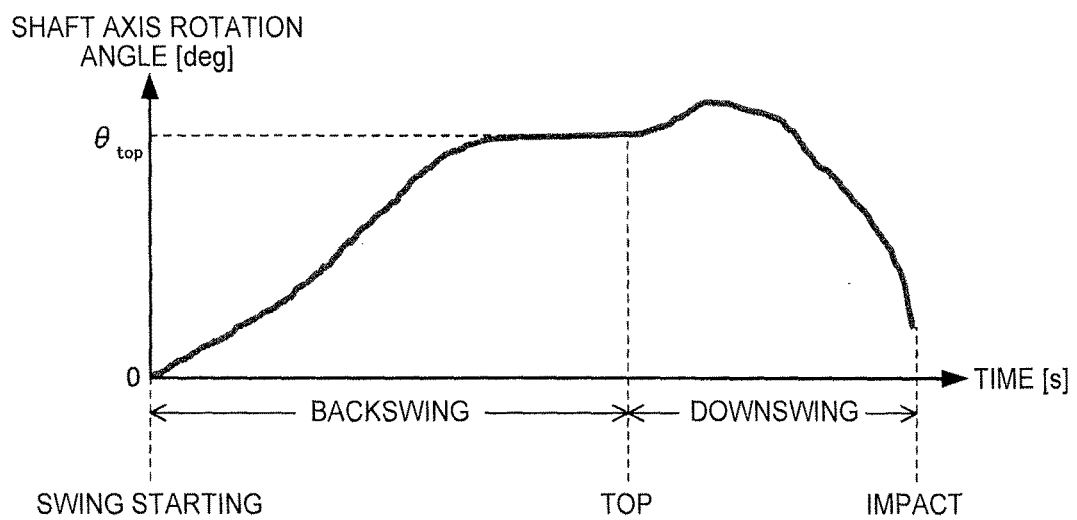
FIG. 13 is a diagram illustrating an example of a temporal change of a shaft axis rotation angle from swing starting (backswing starting) to impact.

FIG. 13 is a diagram illustrating an example of a temporal change of the shaft axis rotation angle from starting of a swing (starting of a backswing) to impact. In FIG. 13, a transverse axis expresses time (s), and a longitudinal axis expresses a shaft axis rotation angle (deg). FIG. 13 illustrates the shaft axis rotation angle $\theta_{top}$ at top with the time of starting a swing (the time of starting a backswing) as a reference timing (at which the shaft axis rotation angle is 0°.

In the present embodiment, as illustrated in FIG. 2, the y axis of the sensor unit 10 substantially matches the long axis direction of the shaft of the golf club 3 (the long axis direction of the golf club 3). Therefore, for example, the swing analysis portion 211 time-integrates a y axis angular velocity included in angular velocity data from the swing starting (backswing starting) time point $t_{start}$ or the time of address to the top time point $t_{top}$ (at top), so as to compute the shaft axis rotation angle $\theta_{top}$.

Calculation of Head Speed

A head speed is the magnitude of a speed of the head at impact (the moment of the impact, right before the impact, or right after the impact). For example, the swing analysis portion 211 computes a speed of the head at the impact time point $t_{impact}$ on the basis of differences between the coordinates of the position of the head at the impact time point $t_{impact}$ and coordinates of a position of the head at the previous time point. The swing analysis portion 211 computes the magnitude of the speed of the head as the head speed.

1-1-4. Score Calculation Process

In the present embodiment, the processing section 21 (particularly, the score calculation portion 212) of the swing diagnosis apparatus 20 performs a process of calculating scores and a total score of predetermined items indicating features of a swing.

The predetermined items which are score calculation targets in the score calculation portion 212 include an item indicating a relationship between a rotation angle about the long axis of the golf club 3 (an example of an exercise appliance) at a predetermined timing between the time of staring a backswing and the time of impact (the time of hitting a ball), and an inclination of the head (an example of a ball hitting portion) of the golf club 3 at impact.

The rotation angle may be an angle by which the golf club 3 is rotated about the long axis from the time of starting the backswing to the predetermined timing. The predetermined timing may be the time (the time of a top) at which the backswing transitions to a downswing. The inclination of the head may be an angle formed between a line of intersection of the face surface (an example of a hitting surface) of the head and a reference plane (for example, the XY plane), and a straight line orthogonal to a target hit ball direction (target line) in the reference plane, that is, may be the face angle ϕ.

Hereinafter, the predetermined items are assumed to include an item (hereinafter, this item will be referred to as a "rotation" item) indicating a relationship between the "shaft axis rotation angle $\theta_{top}$ at top" which is an index based on the rotation angle about the long axis of the golf club 3 at the top timing, and the "face angle ϕ" which is an index based on the inclination of the head at impact.

The predetermined items may include an item regarding a speed of the golf club 3 at impact (at ball hitting). Hereinafter, the predetermined items are assumed to include an item (hereinafter, this item will be referred to as a "speed" item) indicating a relationship among a "head speed" which is an index based on the speed of the golf club 3 at impact, a "sex", and the "type of golf club 3".

A detailed description will be made of a method of calculating a score of each item and a method of calculating a total score in the score calculation portion 212 of the processing section 21.

Calculation of Score of "Rotation" Item

The score calculation portion 212 calculates a score of the "rotation" item depending on in which range among a plurality of ranges each of the shaft axis rotation angle $\theta_{top}$ at top and the face angle ϕ is included. Specifically, first, the score calculation portion 212 determines in which range each of the shaft axis rotation angle $\theta_{top}$ at top and the face angle ϕ included in data (selected swing analysis data 244) regarding a swing is included. Next, the score calculation portion 212 calculates a score corresponding to a determination result by referring to the rotation score table 245.

In the present embodiment, as illustrated in FIG. 14A, the rotation score table 245 defines a score for each combination of a range in which the shaft axis rotation angle $\theta_{top}$ at top is included and a range in which the face angle ϕ is included. In the example illustrated in FIG. 14A, a range in which the shaft axis rotation angle $\theta_{top}$ at top is included is classified into five ranges such as "less than θ1", "θ1 or more and less than θ2", "θ2 or more and less than θ3", "θ3 or more and less than θ4", and "θ4 or more". A range in which the face angle ϕ is included is classified into seven ranges such as "less than ϕ1", "ϕ1 or more and less than ϕ4", "ϕ2 or more and less than ϕ3", "ϕ3 or more and less than ϕ4", "ϕ4 or more and less than ϕ4", "ϕ5 or more and less than ϕ6", and "ϕ6 or more". For example, in a case where the shaft axis rotation angle $\phi_{top}$ at top is included in the range of "less than θ1", and the face angle ϕ is included in the range of "less than θ1", a score is pr1. Each of scores pr1 to pr35 illustrated in FIG. 14A is any one of, for example, 1 point to 5 points.

The score calculation portion 212 may calculate a lower score as a hit ball predicted on the basis of a relationship between the shaft axis rotation angle $\theta_{top}$ at top and the face angle ϕ becomes more easily curved. The term "easily curved" may indicate that a trajectory after ball hitting is easily curved (easily sliced or hooked), and may indicate that a hit ball direction is easily deviated relative to a target direction (target line). Alternatively, the score calculation portion 212 may calculate a higher score as a hit ball more easily flies straight. The term "easily flies straight" may indicate that a trajectory after ball hitting is hardly curved (easily straightened), and may indicate that a hit ball direction is hardly deviated relative to a target direction (target line).

For example, since the face surface of the golf club 3 is considerably open in a state where the shaft axis rotation angle $\theta_{top}$ at top is extremely large, it is expected that the face surface is not completely returned to a square at impact, and thus a hit ball is easily curved. A state in which the face angle ϕ is extremely large is a state in which the face surface at impact is considerably open, and a state in which the face angle ϕ is extremely small (a negative state in which an absolute value thereof is great) is a state in which the face surface at impact is considerably closed. In either state, it is expected that a hit ball is easily curved. In other words, for example, in a case where the shaft axis rotation angle $\theta_{top}$ is included in the range of "θ4 or more", and the face angle ϕ is included in the range of "less than φ1" or "φ6 or more", it is expected that a hit ball is easily curved, and thus the score calculation portion 212 calculates a relatively low score. Therefore, in the example illustrated in FIG. 14A, pr29 or pr35 may be 1 point which is the lowest score, for example, among 1 point to 5 points.

For example, if the shaft axis rotation angle $\theta_{top}$ at top is small, it is expected that the face surface is completely returned to the square at impact, and thus a hit ball easily flies straight. If the face angle φ is close to 0°, the face surface at impact is close to the square, and thus it is expected that a hit ball easily flies straight. In other words, in a case where the shaft axis rotation angle $\theta_{top}$ is included in the range of "less than θ1", and the face angle φ is included in the range of "θ3 or more and less than θ4", it is expected that a hit ball easily flies straight, and thus the score calculation portion 212 calculates a relatively high score (for example, 5 points maximum). Therefore, in the example illustrated in FIG. 14A, pr4 may be 5 points which is the highest score, for example, among 1 point to 5 points.

The swing diagnosis apparatus 20 may not only display a score of the "rotation" item but may also present information regarding a tendency in the swing of the user 2 associated therewith. For example, the swing diagnosis apparatus 20 specifies a tendency of an impact zone according to a combination of the shaft axis rotation angle $\theta_{top}$ at top and the face angle φ obtained through the swing of the user 2, by referring to a table defining a tendency of the impact zone for each combination of a range in which the shaft axis rotation angle $\theta_{top}$ at top is included and a range in which the face angle φ is included as illustrated in FIG. 14B. In the above-described manner, the swing diagnosis apparatus 20 can present a tendency of the impact zone on the basis of a value of shaft axis rotation linked with the face.

Calculation of Score of "Speed" Item

The score calculation portion 212 calculates a score of the "speed" item depending on in which range among a plurality of ranges a head speed is included. However, a head speed differs depending on males and females, and, generally, there is a tendency that a head speed of the males is high. A head speed differs depending on a driver or an iron, and, generally, there is a tendency that a head speed of the driver is high. Thus, it is preferable to select of a plurality of set ranges for classifying a head speed on the basis of the sex or the type of golf club. Specifically, first, the score calculation portion 212 determines whether the user 2 is a male or a female, and whether the golf club 3 which is used is a driver or an iron, on the basis of information regarding the sex of the user 2 and information regarding the type of golf club 3 included in data (selected swing analysis data 244 or the like) regarding a swing. Then, the score calculation portion 212 selects a plurality of set ranges for classifying a head speed on the basis of a determination result. Next, the score calculation portion 212 determines in which range among a plurality of ranges a head speed included in the swing analysis data 244 is included. Next, the score calculation portion 212 calculates a score corresponding to the determination result by referring to the speed score table 246. The score calculation portion 212 may calculate a lower score as a head speed becomes lower.

In the present embodiment, as illustrated in FIG. 15, the speed score table 246 defines a plurality of ranges which are set depending on a "male" or a "female", and a "driver" or an "iron", and a score of a range in which a head speed is included for each of the plurality of set ranges. In the example illustrated in FIG. 15, in a case of a "male" and a "driver", a range in which a head speed is included is classified into five ranges such as "less than vh1", "vh1 or more and less than vh2", "vh2 or more and less than vh3", "vh3 or more and less than vh4", and "vh4 or more". In a case of a "male" and an "iron", a range in which a head speed is included is classified into five ranges such as "less than vh5", "vh5 or more and less than vh6", "vh6 or more and less than vh7", "vh7 or more and less than vh8", and "vh8 or more". In a case of a "female" and a "driver", a range in which a head speed is included is classified into five ranges such as "less than vh11", "vh11 or more and less than vh12", "vh12 or more and less than vh13", "vh13 or more and less than vh14", and "vh14 or more". In a case of a "female" and an "iron", a range in which a head speed is included is classified into five ranges such as "less than vh15", "vh15 or more and less than vh16", "vh16 or more and less than vh17", "vh17 or more and less than vh18", and "vh18 or more". For example, in a case of a "male" and a "driver", if a head speed is included in the range of "less than vh1", a score is 1 point which is the lowest score among 1 point to 5 points. If a head speed is included in the range of "vh4 or more", a score is 5 points which is the highest score among 1 point to 5 points. For example, in a case of a "female" and an "iron", if a head speed is included in the range of "less than vh15", a score is 1 point which is the lowest score among 1 point to 5 points. If a head speed is included in the range of "vh18 or more", a score is 5 points which is the highest score among 1 point to 5 points.

Calculation of Total Score

The score calculation portion 212 calculates a total score on the basis of the score of the "rotation" item and the score of the "speed" item.

For example, in a case where a score of each item is 5 points maximum, if a maximum of a total score is 100 points, the score calculation portion 212 may multiply the score of each item by 10 so that 50 points maximum is obtained, and may add all the scores together so as to calculate a total score. In the swing diagnosis screen illustrated in FIG. 6, a score of 5 points maximum of each item is displayed as a radar chart, and the score of each item is multiplied by 10, and 70 points obtained by adding all the scores together is a total score.

For example, the score calculation portion 212 may increase a weight of a highly important item in diagnosis (evaluation) of a swing and may add scores of the items together so as to calculate a total score.

1-1-5. Procedures of Swing Diagnosis Process

Figure 16:
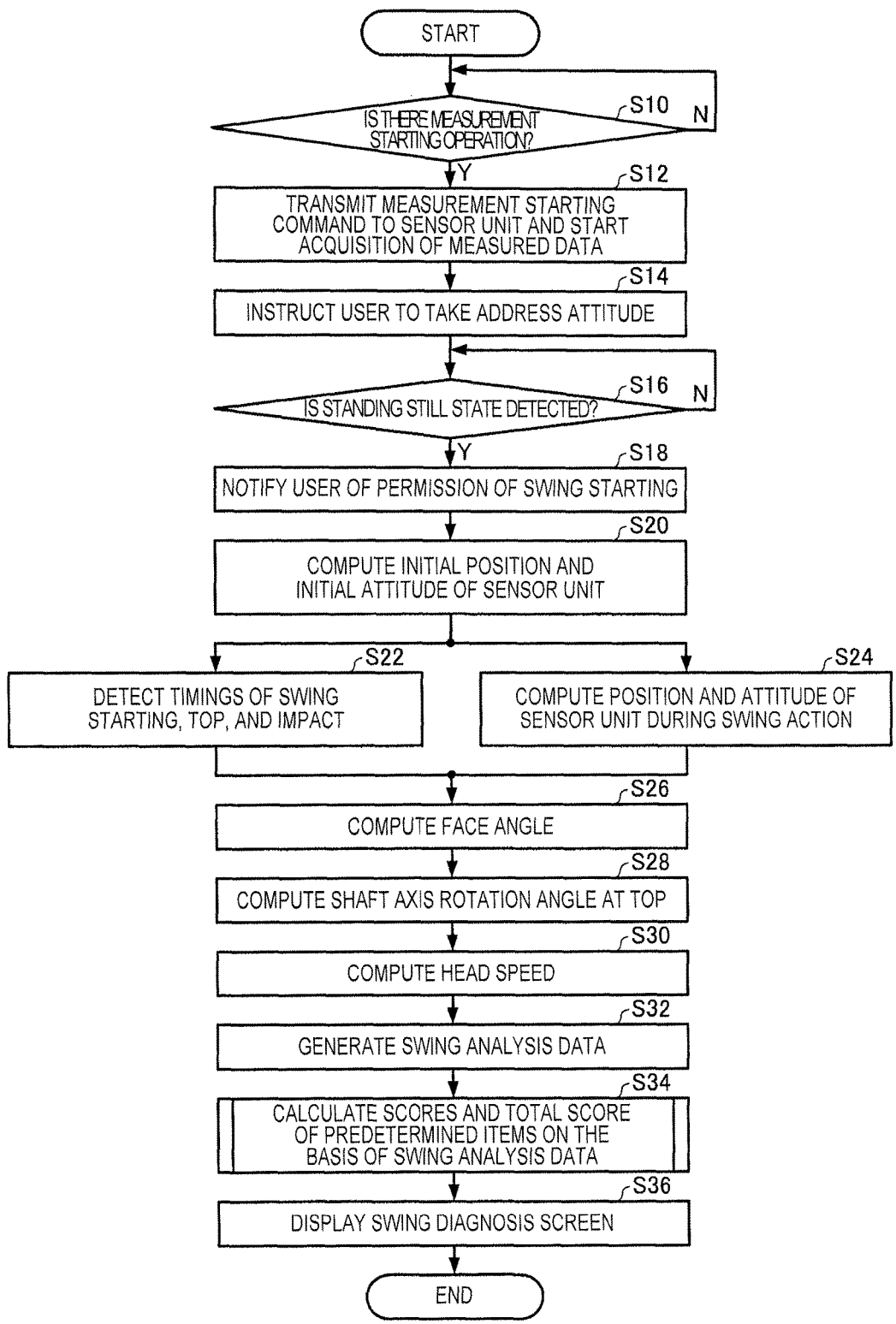
FIG. 16 is a flowchart illustrating examples of procedures of a swing diagnosis process (swing diagnosis method) of the first embodiment.

FIG. 16 is a flowchart illustrating examples of procedures of a swing diagnosis process (swing diagnosis method) performed by the processing section 21. The processing section 21 (an example of a computer) performs the swing diagnosis process, for example, according to the procedures of the flowchart of FIG. 16 by executing the swing diagnosis program 240 stored in the storage section 24. Hereinafter, the flowchart of FIG. 16 will be described.

First, the processing section 21 waits for the user 2 to perform a measurement starting operation (the operation in step S2 in FIG. 3) (N in step S10), transmits a measurement starting command to the sensor unit 10 if the measurement starting operation is performed (Y in step S10), and starts to acquire measured data from the sensor unit 10 (step S12).

Next, the processing section 21 instructs the user 2 to take an address attitude (step S14). The user 2 takes the address attitude in response to the instruction, and stands still (step S4 in FIG. 3).

Next, if a standing still state of the user 2 is detected by using the measured data acquired from the sensor unit 10 (Y in step S16), the processing section 21 notifies the user 2 of permission of swing starting (step S18). The processing section 21 outputs, for example, a predetermined sound, or an LED is provided in the sensor unit 10, and the LED is lighted, so that the user 2 is notified of permission of swing starting. The user 2 confirms the notification and then starts a swing action (the action in step S6 in FIG. 3).

Next, the processing section 21 performs processes in step S20 and subsequent steps after completion of the swing action of the user 2, or from before completion of the swing action.

First, the processing section 21 computes an initial position and an initial attitude of the sensor unit 10 by using the measured data (measured data during standing still (at address) of the user 2) acquired from the sensor unit 10 (step S20).

Next, the processing section 21 detects a swing starting timing, a top timing, and an impact timing by using the measured data acquired from the sensor unit 10 (step S22).

The processing section 21 computes a position and an attitude of the sensor unit 10 during the swing action of the user 2 in parallel to the process in step S22, or before and after the process in step S22 (step S24).

Next, in steps S26 to S30, the processing section 21 computes values of various indexes regarding the swing by using at least some of the measured data acquired from the sensor unit 10, the swing starting, top and impact timings detected in step S22, and the position and the attitude of the sensor unit 10 computed in step S24.

The processing section 21 computes the face angle φ in step S26.

The processing section 21 computes the shaft axis rotation angle $\theta_{top}$ at top in step S28.

The processing section 21 computes a head speed in step S30.

The processing section 21 generates the swing analysis data 244 by using the various indexes calculated in steps S26 to S30 (step S32).

The processing section 21 calculates scores and a total score of predetermined items on the basis of the swing analysis data generated in step S32 (step S34).

The processing section 21 displays the swing diagnosis screen (FIG. 6) on the display section 25 on the basis of information regarding the scores and total score of the predetermined items calculated in step S34 (step S36), and finishes the swing diagnosis process.

In the flowchart of FIG. 16, order of the respective steps may be changed as appropriate within an allowable range, some of the steps may be omitted or changed, and other steps may be added thereto.

Figure 17:
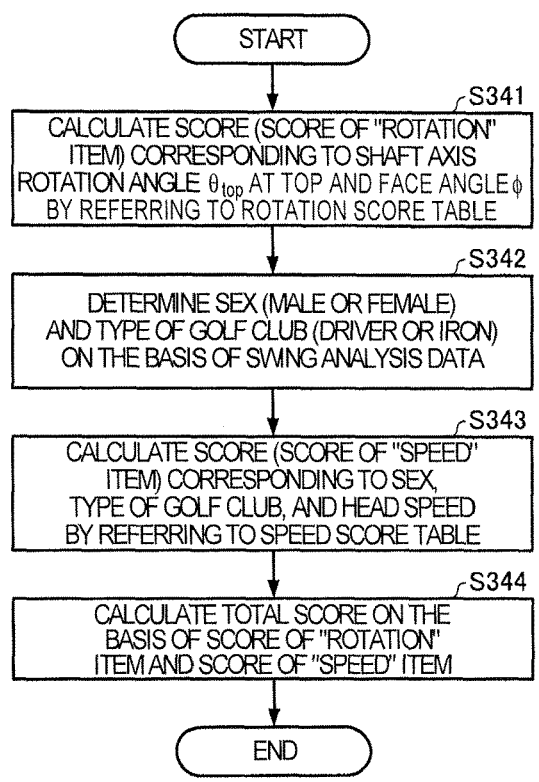
FIG. 17 is a flowchart illustrating examples of procedures of a process of calculating scores and a total score of predetermined items.

FIG. 17 is a flowchart illustrating examples of procedures of a process (step S34 in FIG. 16) of calculating scores and a total score of predetermined items in the processing section 21 (score calculation portion 212). Hereinafter, the flowchart of FIG. 17 will be described.

First, the processing section 21 calculates a score (a score of the "rotation" item) corresponding to the shaft axis rotation angle $\theta_{top}$ at top and the face angle φ by referring to the rotation score table 245 stored in the storage section (step S341).

Next, the processing section 21 determines the sex (a male or a female) and the type of golf club (a driver or an iron) on the basis of the swing analysis data 244 (step S342).

Next, the processing section 21 calculates a score (a score of the "speed" item) corresponding to the sex, the type of golf club, and a head speed by referring to the speed score table 246 stored in the storage section 24 (step S343).

Finally, the processing section 21 calculates a total score on the basis of the score of the "rotation" item calculated in step S341 and the score of the "speed" item calculated in step S343 (step S344).

1-1-6. Operations and Effects

As described above, according to the swing diagnosis system 1 of the first embodiment, the swing diagnosis apparatus 20 calculates scores on the basis of a relationship between a rotation angle about the long axis of the golf club 3 at a desired timing during a swing and an inclination of the head of the golf club 3 at impact and displays the scores on the display section 25, on the basis of the swing analysis data 244 generated by using measured data in the sensor unit 10, and can thus digitalize (level) features of the swing till the impact.

Particularly, according to the swing diagnosis system 1 of the first embodiment, the swing diagnosis apparatus 20 can digitalize and clearly show features of the swing based on a relationship between the shaft axis rotation angle $\theta_{top}$ at top and the face angle φ by using a score of the "rotation" item. For example, the swing diagnosis apparatus 20 calculates a lower score as a hit ball becomes more easily curved with respect to the "rotation" item, and can thus digitalize and clearly show features of the swing till the impact according to the extent to which a hit ball is easily curved.

According to the swing diagnosis system 1 of the first embodiment, the swing diagnosis apparatus 20 can digitalize and clearly show features of the swing based on a speed of the head of the golf club 3 at impact by using a score of the "speed" item. For example, the swing diagnosis apparatus 20 calculates a lower score as a speed of the head is lowered with respect to the "speed" item, and can thus digitalize and clearly show features of the swing according to the speed of the head at impact.

Therefore, the user 2 can recognize a level of the swing, strong points, weak points, problems, and the like in the swing thereof by using the scores of the "rotation" item and the "speed" item obtained as diagnosis results based on the swing analysis data 244.

According to the swing diagnosis system 1 of the first embodiment, since the swing analysis process and the swing diagnosis process are performed by using the sensor unit 10, a large apparatus such as a camera is not required to be used, and there is less restriction in a location where the user 2 performs a swing.

1-2. Second Embodiment

In a second embodiment, the same constituent elements as those in the first embodiment are given the same reference numerals, description of the content overlapping the first embodiment will be omitted or will be made briefly, and the content different from the first embodiment will be described.

1-2-1. Configuration of Swing Diagnosis System

Figure 18:
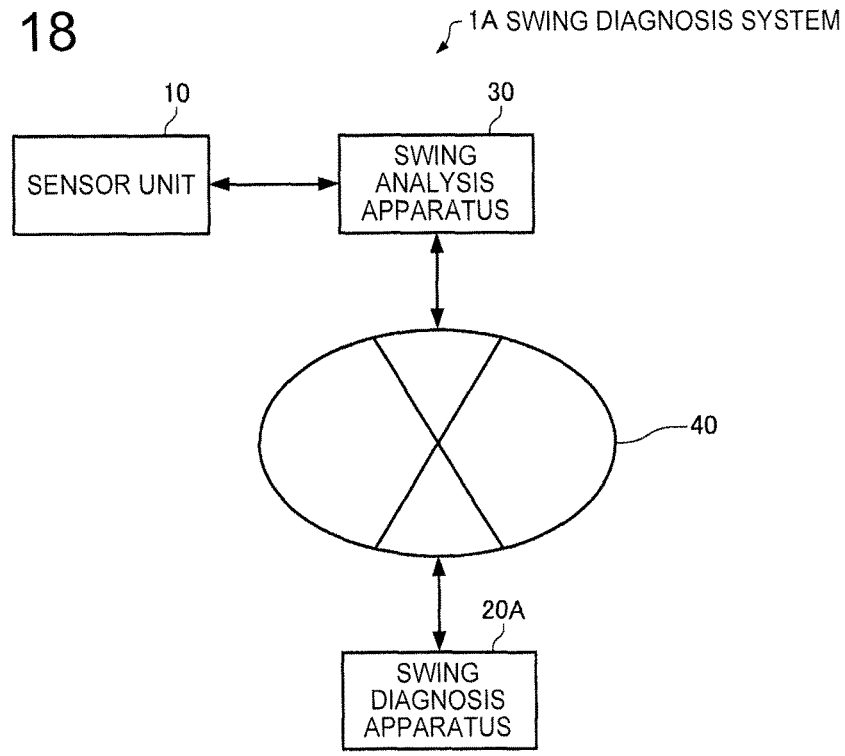
FIG. 18 is a diagram illustrating a configuration example of a swing diagnosis system of a second embodiment.

FIG. 18 is a diagram illustrating a configuration example of a swing diagnosis system according to the second embodiment. As illustrated in FIG. 18, a swing diagnosis system 1A of the second embodiment is configured to include a sensor unit 10, a swing analysis apparatus 30, and a swing diagnosis apparatus 20A.

If a user 2 performs the measurement starting operation in step S2 in FIG. 3, the swing analysis apparatus 30 transmits a measurement starting command to the sensor unit 10, and the sensor unit 10 receives the measurement starting command and starts measurement of three-axis accelerations and three-axis angular velocities. Communication between the sensor unit 10 and the swing analysis apparatus 30 may be wireless communication, and may be wired communication.

The swing analysis apparatus 30 notifies the user 2 of permission of swing starting, shown in step S5 in FIG. 3, and then analyzes the swing action (step S6 in FIG. 3) in which the user 2 has hit the ball by using the golf club 3.

The swing analysis apparatus 30 generates swing analysis data including information regarding a time point (date and time) at which the swing is performed, identification information or the sex of the user 2, the type of golf club 3, and an analysis result of the swing action, and transmits the swing analysis data to the swing diagnosis apparatus 20A via a network 40 (refer to FIG. 18).

The swing diagnosis apparatus 20A receives the swing analysis data transmitted by the swing analysis apparatus 30 via the network 40, and preserves the swing analysis data. Therefore, whenever the user 2 performs a swing action according to the procedures illustrated in FIG. 3, the swing analysis data generated by the swing analysis apparatus 30 is preserved in the swing diagnosis apparatus 20A, and thus a swing analysis data list is built.

For example, the swing analysis apparatus 30 may be implemented by an information terminal (client terminal) such as a smart phone or a personal computer, and the swing diagnosis apparatus 20A may be implemented by a server which processes requests from the swing analysis apparatus 30.

The network 40 may be a wide area network (WAN) such as the Internet, and may be a local area network (LAN). The swing analysis apparatus 30 and the swing diagnosis apparatus 20A may communicate with each other through, for example, near field communication or wired communication, without using the network 40.

In the present embodiment, if the user 2 activates a swing diagnosis application via an operation section 23 (refer to FIG. 19) of the swing analysis apparatus 30, the swing analysis apparatus 30 performs communication with the swing diagnosis apparatus 20A, and, for example, a selection screen of swing analysis data is displayed on the display section 25 of the swing analysis apparatus 30. The selection screen includes a list of the swing analysis data for the user 2 included in the swing analysis data list preserved in the swing diagnosis apparatus 20A. The user selects any one of the items of swing analysis data from the list of the swing analysis data via an operation of the swing analysis apparatus 30. Consequently, the swing analysis apparatus 30 transmits selected information of the swing analysis data to the swing diagnosis apparatus 20A.

The swing diagnosis apparatus 20A receives the selected information, and calculates scores of predetermined items by using the selected swing analysis data. Specifically, in the same manner as in the first embodiment, the swing diagnosis apparatus 20A calculates scores of respective two items such as a "rotation" item and a "speed" item (5 points maximum). The swing diagnosis apparatus 20A may calculate a total score of the swing by using the scores of the two items. The swing diagnosis apparatus 20A transmits information regarding the calculated scores and total score of the predetermined items to the swing analysis apparatus 30.

The swing analysis apparatus 30 receives the information regarding the scores and total score of the predetermined items and displays a swing diagnosis screen as illustrated in FIG. 6 on the display section 25. The user 2 can understand scores and a total score of a plurality of items as diagnosis results for the swing analysis data on the left part on the basis of the swing diagnosis screen illustrated in FIG. 6. Particularly, if the user 2 can understand strong points or weak points in the user's swing on the basis of the swing diagnosis screen illustrated in FIG. 6.

1-2-2. Configuration of Sensor Unit and Swing Analysis Apparatus

Figure 19:
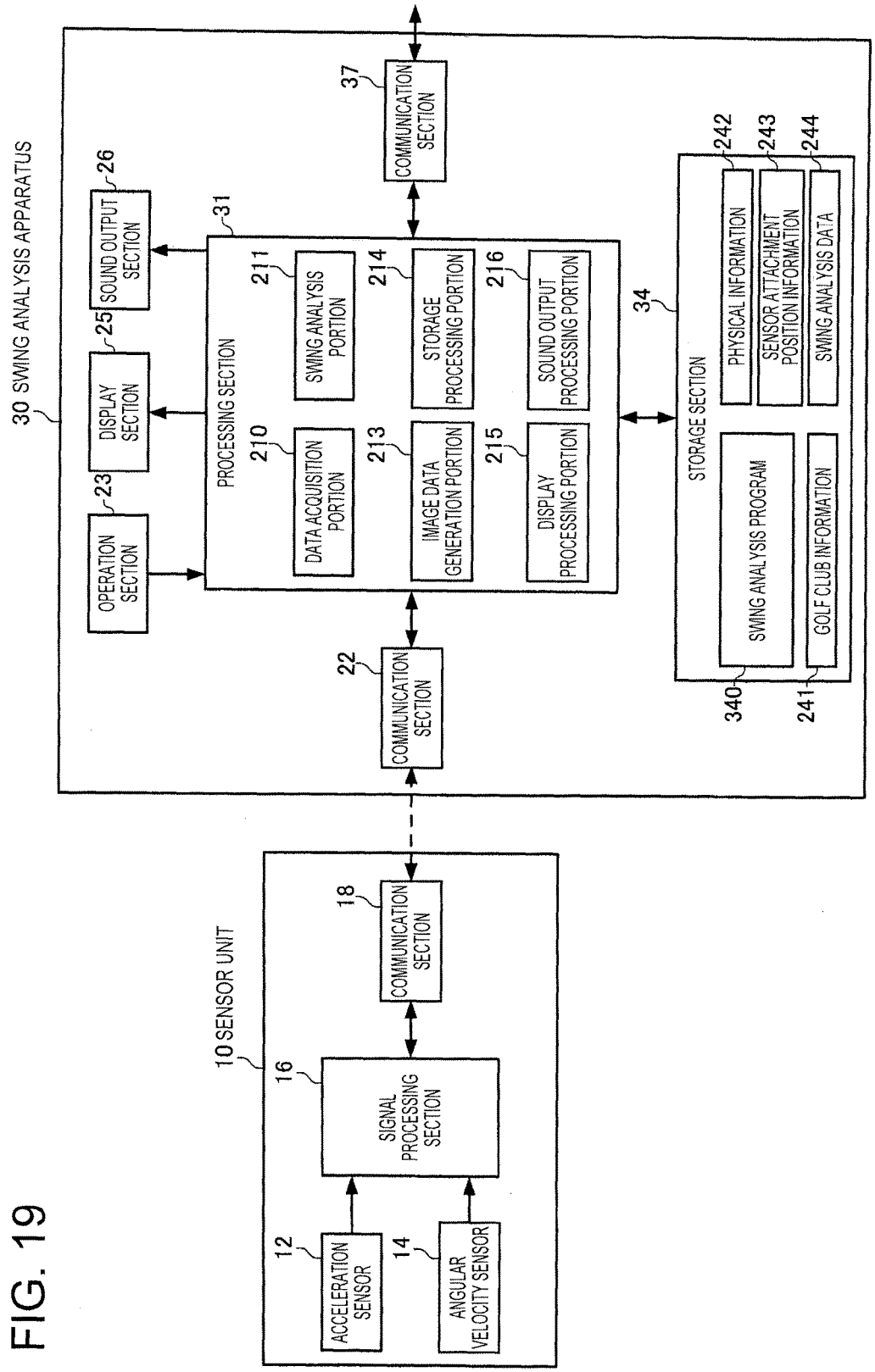
FIG. 19 is a diagram illustrating configuration examples of a sensor unit and a swing analysis apparatus of the second embodiment.

FIG. 19 is a diagram illustrating configuration examples of the sensor unit 10 and the swing analysis apparatus 30. As illustrated in FIG. 19, a configuration and a function of the sensor unit 10 are the same as those in the first embodiment, and thus description thereof will be omitted.

The swing analysis apparatus 30 is configured to include a processing section 31, the communication section 22, the operation section 23, the storage section 34, the display section 25, the sound output section 26, and a communication section 37. However, the swing analysis apparatus 30 may have a configuration in which some of the constituent elements are deleted or changed as appropriate, or may have a configuration in which other constituent elements are added thereto. Configurations and functions of the communication section 22, the operation section 23, the display section 25, and the sound output section 26 are the same as those in the first embodiment, and thus description thereof will be omitted.

The storage section 34 is constituted of, for example, various IC memories such as a read only memory (ROM), a flash ROM, and a random access memory (RAM), or a recording medium such as a hard disk or a memory card. The storage section 34 stores a program for the processing section 31 performing various calculation processes or a control process, or various programs or data for realizing application functions.

In the present embodiment, the storage section 34 stores a swing analysis program 340 which is read by the processing section 31 is used for executing a swing analysis process. The swing analysis program 340 may be stored in a nonvolatile recording medium (computer readable recording medium) in advance, or the swing analysis program 340 may be received from a server (not illustrated) or the swing diagnosis apparatus 20A by the processing section 31 via a network, and may be stored in the storage section 34.

The storage section 34 stores golf club information 241, physical information 242, sensor attachment position information 243, and swing analysis data 244.

The storage section 34 is used as a work area of the processing section 31, and temporarily stores data which is input from the operation section 23, results of calculation executed by the processing section 31 according to various programs, and the like. The storage section 34 may store data which is required to be preserved for a long period of time among data items generated through processing of the processing section 31.

The communication section 37 performs data communication with a communication section 27 (refer to FIG. 20) of the swing diagnosis apparatus 20A via the network 40. For example, the communication section 37 performs a process of receiving the swing analysis data 244 from the processing section 31 after a swing analysis process is completed, and transmitting the swing analysis data to the communication section 27 of the swing diagnosis apparatus 20A. For example, the communication section 37 performs a process of receiving information required to display the selection screen of the swing analysis data from the communication section 27 of the swing diagnosis apparatus 20A and transmitting the information to the processing section 31, and a process of receiving selected information on the selection screen from the processing section 31 and transmitting the selected information to the communication section 27 of the swing diagnosis apparatus 20A. For example, the communication section 37 performs a process of receiving information (diagnosis result information (scores or a total score of predetermined items) based on the selected swing analysis data) required to display the swing diagnosis screen illustrated in FIG. 6 from the communication section 27 of the swing diagnosis apparatus 20A, and transmitting the information to the processing section 31.

The processing section 31 performs a process of transmitting a control command to the sensor unit 10 via the communication section 22, or various computation processes on data which is received from the sensor unit 10 via the communication section 22, according to various programs. The processing section 31 performs a process of reading the swing analysis data 244 from the storage section 34, and transmitting the swing analysis data to the swing diagnosis apparatus 20A via the communication section 37, according to various programs. The processing section 31 performs a process of transmitting the selected information of the swing analysis data to the swing diagnosis apparatus 20A via the communication section 37, and displaying the swing diagnosis screen illustrated in FIG. 6 on the basis of the information received from the swing diagnosis apparatus 20A, according to various programs. The processing section 31 performs other various control processes.

Particularly, in the present embodiment, by executing the swing analysis program 340, the processing section 31 functions as a data acquisition portion 210, a swing analysis portion 211, an image data generation portion 213, a storage processing portion 214, a display processing portion 215, and a sound output processing portion 216, and performs a process (swing analysis process) of analyzing a swing action of the user 2. Configurations and functions of the data acquisition portion 210, the swing analysis portion 211, the image data generation portion 213, the storage processing portion 214, the display processing portion 215, and the sound output processing portion 216 are the same as those in the first embodiment, and thus description thereof will be omitted. The swing analysis process is also the same as that in the first embodiment, and thus description thereof will be omitted.

1-2-3. Configuration of Swing Diagnosis Apparatus

Figure 20:
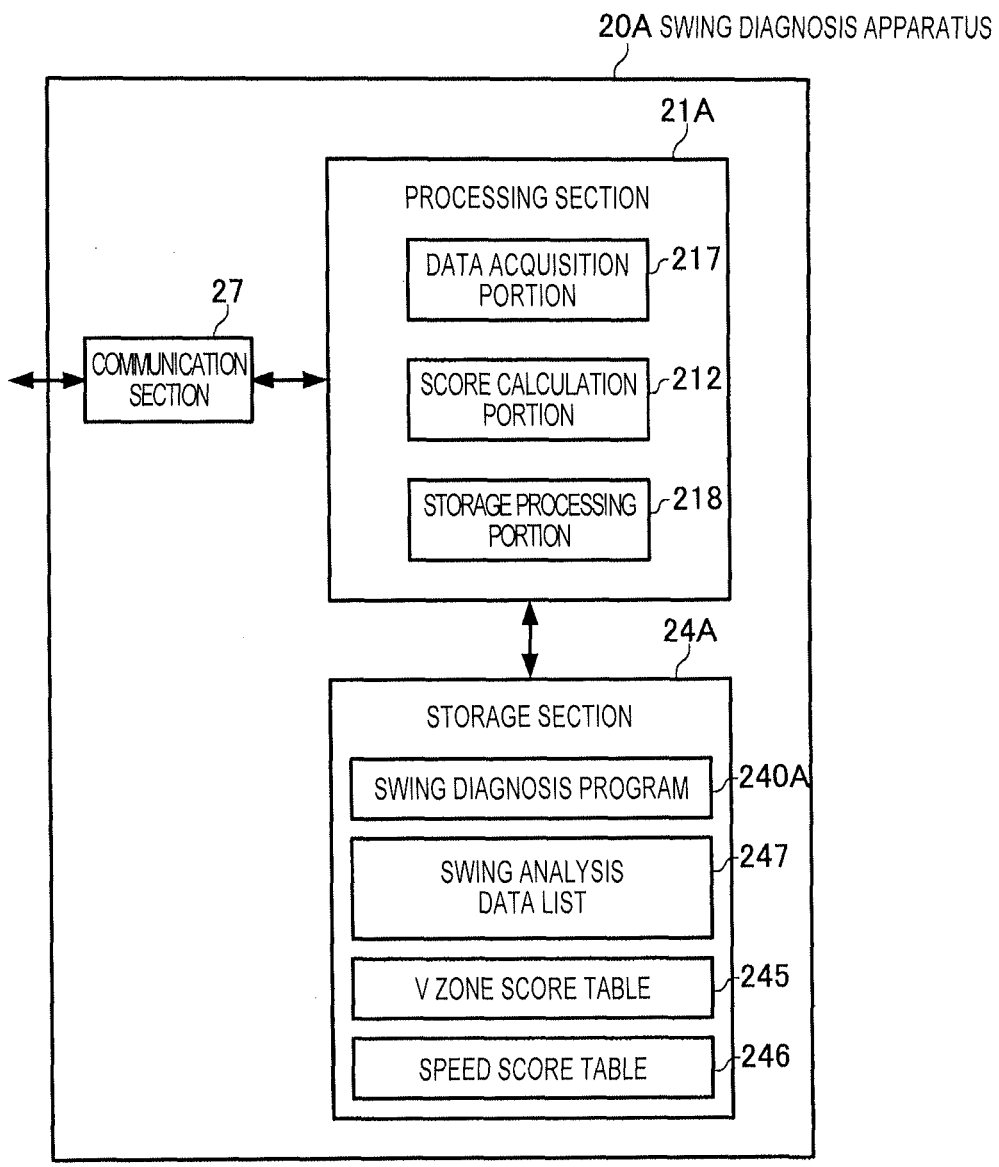
FIG. 20 is a diagram illustrating a configuration example of a swing diagnosis apparatus of the second embodiment.

FIG. 20 is a diagram illustrating a configuration example of the swing diagnosis apparatus 20A. As illustrated in FIG. 20, in the present embodiment, the swing diagnosis apparatus 20A is configured to include a processing section 21A, the communication section 27, and a storage section 24A. However, the swing diagnosis apparatus 20A may have a configuration in which some of the constituent elements are deleted or changed as appropriate, or may have a configuration in which other constituent elements are added thereto.

The storage section 24A is constituted of, for example, various IC memories such as a ROM, a flash ROM, and a RAM, or a recording medium such as a hard disk or a memory card. The storage section 24A stores a program for the processing section 21A performing various calculation processes or a control process, or various programs or data for realizing application functions.

In the present embodiment, the storage section 24A stores a swing diagnosis program 240A which is read by the processing section 21A and is used for executing a swing diagnosis process. The swing diagnosis program 240A may be stored in a nonvolatile recording medium (computer readable recording medium) in advance, or the swing diagnosis program 240A may be received from a server (not illustrated) by the processing section 21A via a network, and may be stored in the storage section 24A.

In the present embodiment, the storage section 24A stores (preserves) a swing analysis data list 247 including a plurality of items of swing analysis data 244 generated by the swing analysis apparatus 30. In other words, the swing analysis data 244 generated whenever the processing section 31 of the swing analysis apparatus 30 analyzes a swing action of the user 2 is sequentially added to the swing analysis data list 247.

In the present embodiment, the storage section 24A stores the rotation score table 245 and the speed score table 246.

The storage section 24A is used as a work area of the processing section 21A, and temporarily stores results of calculation executed by the processing section 21A according to various programs, and the like. The storage section 24A may store data which is required to be preserved for a long period of time among data items generated through processing of the processing section 21A.

The communication section 27 performs data communication with the communication section 37 (refer to FIG. 19) of the swing analysis apparatus 30 via the network 40. For example, the communication section 27 performs a process of receiving the swing analysis data 244 from the communication section 37 of the swing analysis apparatus 30, and transmitting the swing analysis data 244 to the processing section 2171. For example, the communication section 27 performs a process of transmitting information required to display the selection screen of the swing analysis data to the communication section 37 of the swing analysis apparatus 30, or a process of receiving selected information on the selection screen of the swing analysis data from the communication section 37 of the swing analysis apparatus 30 and transmitting the selected information to the processing section 21A. For example, the communication section 27 performs a process of receiving diagnosis result information (scores or a total score of predetermined items) based on the swing analysis data 244 selected according to the selected information from the processing section 21A, and transmitting the information to the communication section 37 of the swing analysis apparatus 30. For example, the communication section 27 performs a process of receiving information required to display the swing diagnosis screen illustrated in FIG. 6 from the processing section 21A and transmitting the information to the communication section 37 of the swing analysis apparatus 30.

The processing section 21A performs a process of receiving the swing analysis data 244 from the swing analysis apparatus 30 via the communication section 27 and storing the swing analysis data 244 in the storage section 24A (adding the swing analysis data to the swing analysis data list 247), according to various programs. The processing section 21A performs a process of receiving selected information from the swing analysis apparatus 30 via the communication section 27, and transmitting information required to display the swing diagnosis screen illustrated in FIG. 6 to the swing analysis apparatus 30, according to various programs. The processing section 21A performs other various control processes.

Particularly, in the present embodiment, the processing section 21A functions as a data acquisition portion 217, the score calculation portion 212, and a storage processing portion 218 by executing the swing diagnosis program 240A, and performs a diagnosis process (swing diagnosis process) on the swing analysis data 244 selected from the swing analysis data list 247.

The data acquisition portion 217 performs a process of receiving the swing analysis data 244 received from the swing analysis apparatus 30 by the communication section 27 and transmitting the swing analysis data 244 to the storage processing portion 218. The data acquisition portion 217 performs a process of receiving various pieces of information received from the swing analysis apparatus 30 by the communication section 27 and transmitting the information to the score calculation portion 212.

The storage processing portion 218 performs read/write processes of various programs or various data for the storage section 24A. The storage processing portion 218 performs a process of receiving the swing analysis data 244 from the data acquisition portion 217 and storing the swing analysis data 244 in the storage section 24A (adding the swing analysis data to the swing analysis data list 247), a process of reading the swing analysis data 244 from the swing analysis data list 247 stored in the storage section 24A, or the like. For example, the storage processing portion 218 performs a process of reading the rotation score table 245 or the speed score table 246 stored in the storage section 24A.

The score calculation portion 212 performs a process of calculating scores of predetermined items on the basis of data regarding a swing. In the present embodiment, the data regarding the swing is the swing analysis data 244 selected based on the selected information. A function of the score calculation portion 212 or a score calculation process performed by the score calculation portion 212 is the same as that in the first embodiment, and thus description thereof will be omitted.

1-2-4. Procedures of Swing Diagnosis Process (Swing Diagnosis Method)

Figure 21:
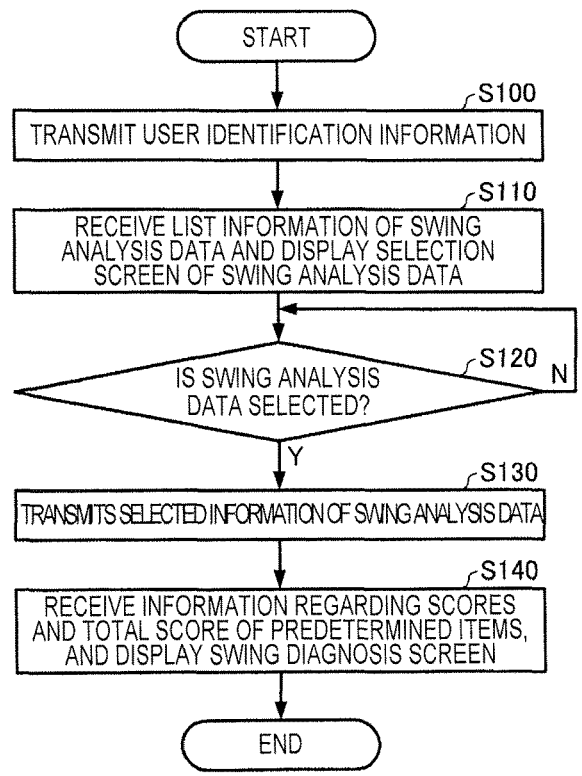
FIG. 21 is a flowchart illustrating examples of procedures of a process performed by the swing analysis apparatus in relation to a swing diagnosis process of the second embodiment.
Figure 22:
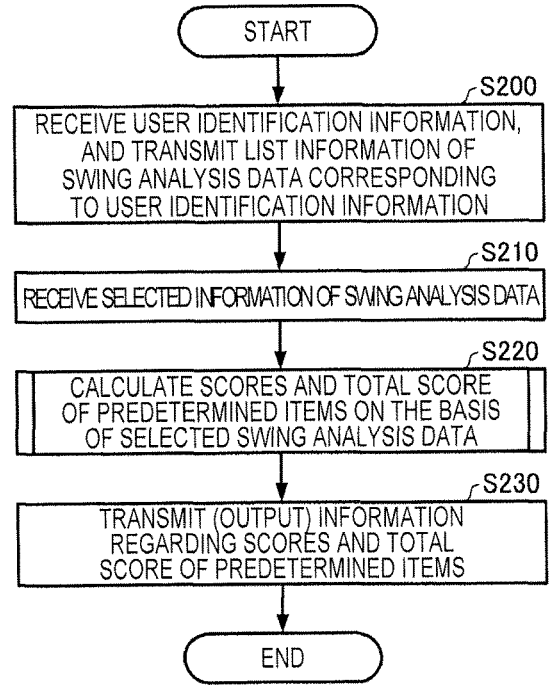
FIG. 22 is a flowchart illustrating examples of procedures of the swing diagnosis process (swing diagnosis method) of the second embodiment.

FIG. 21 is a flowchart illustrating examples of procedures of a process performed by the processing section 31 of the swing analysis apparatus 30 in relation to the swing diagnosis process. FIG. 22 is a flowchart illustrating examples of procedures of the swing diagnosis process (swing diagnosis method) performed by the processing section 21A of the swing diagnosis apparatus 20A. The processing section 21A (an example of a computer) of the swing diagnosis apparatus 20A performs the swing diagnosis process, for example, according to the procedures of the flowchart of FIG. 22 by executing the swing diagnosis program 240A stored in the storage section 24A. Hereinafter, the flowcharts of FIGS. 21 and 22 will be described.

First, the processing section 31 of the swing analysis apparatus 30 transmits user identification information allocated to the user 2, to the swing diagnosis apparatus 20A (step S100 in FIG. 21).

Next, the processing section 21A of the swing diagnosis apparatus 20A receives the user identification information, and transmits list information of the swing analysis data 244 corresponding to the user identification information (step S200 in FIG. 22).

Next, the processing section 31 of the swing analysis apparatus 30 receives the list information of the swing analysis data 244, and displays a selection screen of the swing analysis data on the display section 25 (step S110 in FIG. 21).

The processing section 31 of the swing analysis apparatus 30 waits for the swing analysis data 244 to be selected on the selection screen of the swing analysis data (N in step S120 in FIG. 21), and transmits selected information of the swing analysis data to the swing diagnosis apparatus 20A (step S130 in FIG. 21) if the information is selected (Y in step S120 in FIG. 21).

Next, the processing section 21A of the swing diagnosis apparatus 20A receives the selected information of the swing analysis data (step S210 in FIG. 22), and calculates scores and a total score of predetermined items on the basis of the swing analysis data 244 which is selected on the basis of the selected information (step S220 in FIG. 22). A detailed procedure in step S220 is the same as the procedure in FIG. 17.

Next, the processing section 21A of the swing diagnosis apparatus 20A transmits (outputs) information regarding the scores and the total score of the predetermined items to the swing analysis apparatus 30 (step S230 in FIG. 22), and finishes the swing diagnosis process.

The processing section 31 of the swing analysis apparatus 30 receives the information regarding the scores and the total score of the predetermined items, displays the swing diagnosis screen (FIG. 6) on the display section 25 (step S140 in FIG. 21), and finishes the process.

In the flowchart of FIG. 21, order of the respective steps may be changed as appropriate within an allowable range, some of the steps may be omitted or changed, and other steps may be added thereto. Similarly, in the flowchart of FIG. 22, order of the respective steps may be changed as appropriate within an allowable range, some of the steps may be omitted or changed, and other steps may be added thereto.

1-2-5. Operations and Effects

As described above, in the swing diagnosis system 1A of the second embodiment, the swing analysis apparatus 30 generates the swing analysis data 244 by using measured data in the sensor unit 10. The swing diagnosis apparatus 20A calculates scores on the basis of a relationship between a rotation angle about the long axis of the golf club 3 at a desired timing during a swing and an inclination of the head of the golf club 3 at impact by using the selected swing analysis data 244. The swing analysis apparatus 30 displays the scores calculated by the swing diagnosis apparatus 20A on the display section 25, and can thus digitalize and visually clearly show features of the swing till the impact.

In the same manner as in the swing diagnosis system 1 of the first embodiment, according to the swing diagnosis system 1A of the second embodiment, it is possible to digitalize and clearly show features of the swing based on a relationship between the shaft axis rotation angle $\theta_{top}$ at top and the face angle $\phi$ by using a score of the "rotation" item.

In the same manner as in the swing diagnosis system 1 of the first embodiment, according to the swing diagnosis system 1A of the second embodiment, it is possible to digitalize and clearly show features of the swing based on a speed of the head of the golf club 3 at impact by using a score of the "speed" item.

Therefore, the user 2 can recognize a level of the swing, strong points, weak points, problems, and the like in the swing thereof by using the scores of the "rotation" item and the "speed" item obtained as diagnosis results based on the swing analysis data 244.

According to the swing diagnosis system 1A of the second embodiment, it is possible to reduce a load on the swing analysis apparatus 30 since the swing diagnosis apparatus 20A performs the swing diagnosis process (score calculation process).

According to the swing diagnosis system 1A of the second embodiment, it is possible to achieve the same effects as in the swing diagnosis system 1 of the first embodiment.

2. Modification Examples

The invention is not limited to the present embodiment, and may be variously modified within the scope of the spirit of the invention.

2-1. Swing Diagnosis System

In the second embodiment, the swing diagnosis apparatus 20A may perform a part of a process (swing analysis process) performed by the swing analysis apparatus 30, and the swing analysis apparatus 30 may perform a part of a process (swing diagnosis process) performed by the swing diagnosis apparatus 20A.

In the second embodiment, the swing diagnosis system 1A may be configured to include a plurality of sensor units 10 and a plurality of swing analysis apparatuses 30.

2-2. Swing Analysis Process

A plurality of sensor units 10 may be attached to the golf club 3 or parts such as the arms or the shoulders of the user 2, and the swing analysis portion 211 may perform a swing analysis process by using measured data from the plurality of sensor units 10.

In the embodiments, the swing analysis portion 211 detects impact by using the square root of the square sum as shown in Equation (2) as a combined value of three-axis angular velocities measured by the sensor unit, but, as a combined value of three-axis angular velocities, for example, a square sum of three-axis angular velocities, a sum or an average of three-axis angular velocities, or the product of three-axis angular velocities may be used. Instead of a combined value of three-axis angular velocities, a combined value of three-axis accelerations such as a square sum or a square root of three-axis accelerations, a sum or an average value of three-axis accelerations, or the product of three-axis accelerations may be used.

2-3. Swing Diagnosis Process

In the respective embodiments, some or all values of indexes included in the swing analysis data 244 may be changed, and the score calculation portion 212 may calculate scores and a total score of predetermined items on the basis of data in which some or all values of the indexes are changed. The score calculation portion 212 may calculate scores and a total score of predetermined items on the basis of data (for example, all indexes are manually input data) in which all values of indexes indicating features of a swing are pseudo-values.

In the embodiments, the score calculation portion 212 calculates scores of two items including the "rotation" item and the "speed" item, but may not calculate a score of the "speed" item, and may calculate scores of other items. In the respective embodiments, the score calculation portion 212 calculates a total score, but may not calculate a total score.

In the respective embodiments, the score calculation portion 212 may calculate scores by using a rotation angle about the shaft axis of the golf club 3 at a desired timing (for example, a halfway back timing or a halfway down timing) other than the top timing instead of the shaft axis rotation angle $\theta_{top}$ at the top. For example, the swing analysis portion 211 may compute a difference $\Delta Z$ between a Z coordinate of a position of the head and a Z coordinate of a position of the grip end at each time point t from a swing start time point $t_{start}$ to an impact time point $t_{impact}$, and may detect a time point $t_{HWB}$ at which a sign of $\Delta Z$ is inversed between the swing start time point $t_{start}$ and the top time point $t_{top}$, as the halfway back timing. The swing analysis portion 211 may detect a time point $t_{HWD}$ at which a sign of $\Delta Z$ is inversed between the top time point $t_{top}$ and the impact time point $t_{impact}$, as the halfway down timing.

In the respective embodiments, the score calculation portion 212 calculates scores of predetermined items by using the score tables, but may use equations instead of the score tables.

In the embodiment, the score calculation portion 212 may also function as the swing analysis portion 211, and may perform a swing diagnosis process (a swing analysis process and a score calculation process) including the swing analysis process on the basis of measured data (an output signal from an inertial sensor) from the sensor unit 10, which is data regarding a swing.

2-4. Others

In the embodiments, the acceleration sensor 12 and the angular velocity sensor 14 are built into and are thus integrally formed as the sensor unit 10, but the acceleration sensor 12 and the angular velocity sensor 14 may not be integrally formed. Alternatively, the acceleration sensor 12 and the angular velocity sensor 14 may not be built into the sensor unit 10, and may be directly mounted on the golf club 3 or the user 2. In the above-described embodiments, the sensor unit 10 and the swing diagnosis apparatus 20 or the swing analysis apparatus 30 are separately provided, but may be integrally formed so as to be attached to the golf club 3 or the user 2. The sensor unit 10 may have some of the constituent elements of the swing diagnosis apparatus 20 or the swing analysis apparatus 30 along with the inertial sensor (for example, the acceleration sensor 12 or the angular velocity sensor 14).

In the embodiments, the swing diagnosis system (swing diagnosis apparatus) diagnosing a golf swing has been exemplified, but the invention is applicable to a swing diagnosis system (swing diagnosis apparatus) diagnosing a swing in various sports such as tennis or baseball.

The above-described embodiments and modification examples are only examples, and the invention is not limited thereto. For example, the embodiments and the respective modification examples may be combined with each other as appropriate.

For example, the invention includes substantially the same configuration (for example, a configuration in which functions, methods, and results are the same, or a configuration in which objects and effects are the same) as the configuration described in the embodiments. The invention includes a configuration in which an inessential part of the configuration described in the embodiments is replaced with another part. The invention includes a configuration which achieves the same operation and effect or a configuration capable of achieving the same object as in the configuration described in the embodiments. The invention includes a configuration in which a well-known technique is added to the configuration described in the embodiments.

The entire disclosure of Japanese Patent Application No. 2015-148640 filed Jul. 28, 2015 is expressly incorporated by reference herein.

What is claimed is:

1. A swing diagnosis apparatus comprising:
a processor programmed to:
   detect, from data collected by one or more sensors, a rotation angle about a rotation axis of an exercise appliance at a predetermined timing between a time of starting a backswing and a time of impact with a longitudinal direction of the exercise appliance as the rotation axis;
   detect a face angle which is an inclination of a ball hitting portion of the exercise appliance at impact; and
   calculate a level of a swing based on a pre-stored rotation score data which defines a score for each combination of one of a plurality of ranges for the rotation angle and one of a plurality of ranges for the face angle.

2. The swing diagnosis apparatus according to claim 1, wherein the rotation angle is an angle by which the exercise appliance is rotated about the rotation axis from the time of starting the backswing to the predetermined timing.

3. The swing diagnosis apparatus according to claim 1, wherein the predetermined timing is a time at which the backswing transitions to a downswing.

4. The swing diagnosis apparatus according to claim 1, wherein the inclination of the ball hitting portion is an angle formed between an outer edge of a hitting surface of the ball hitting portion and a virtual straight line orthogonal to a target hit ball direction in a plan view.

5. The swing diagnosis apparatus according to claim 1, wherein the processor is programmed to calculate the level according to a curved state of a hit ball predicted based on a relationship between the detected rotation angle and the detected face angle.

6. The swing diagnosis apparatus according to claim 1, wherein the processor is programmed to calculate the level based on a speed of the ball hitting portion at impact.

7. The swing diagnosis apparatus according to claim 6, wherein the processor is programmed to calculate the level according to the speed.

8. The swing diagnosis apparatus according to claim 1, further comprising:
a display that displays the calculated level.

9. The swing diagnosis apparatus according to claim 1, wherein the level is a score.

10. A swing diagnosis system comprising:
the swing diagnosis apparatus according to claim 1; and
the one or more sensors including an inertial sensor,
   wherein the processor is programmed to calculate the level based on outputs from the inertial sensor.

11. A swing diagnosis method comprising:
detecting, from data collected by one or more sensors, a rotation angle about a rotation axis of an exercise appliance at a predetermined timing between a time of starting a backswing and a time of impact with a longitudinal direction of the exercise appliance as the rotation axis;
detecting a face angle which is an inclination of a ball hitting portion of the exercise appliance at impact; and
calculating a level of a swing based on a pre-stored rotation score data which defines a score for each combination of one of a plurality of ranges for the rotation angle and one of a plurality of ranges for the face angle.

12. A non-transitory recording medium recording a swing diagnosis program causing a computer to execute:
detecting, from data collected by one or more sensors, a rotation angle about a rotation axis of an exercise appliance at a predetermined timing between a time of starting a backswing and a time of impact with a longitudinal direction of the exercise appliance as the rotation axis;
detecting a face angle which is an inclination of a ball hitting portion of the exercise appliance at impact; and
calculating a level of a swing based on a pre-stored rotation score data which defines a score for each combination of one of a plurality of ranges for the rotation angle and one of a plurality of ranges for the face angle.

13. A swing diagnosis apparatus that:
detects, from data collected by one or more sensors, a rotation angle about a rotation axis of an exercise appliance at a predetermined timing between a time of starting a backswing and a time of impact with a longitudinal direction of the exercise appliance as the rotation axis;
detects a face angle which is an inclination of a ball hitting portion of the exercise appliance at impact; and
calculates a level of a swing based on a pre-stored rotation score data which defines a score for each combination of one of a plurality of ranges for the rotation angle and one of a plurality of ranges for the face angle.

14. The swing diagnosis apparatus according to claim 13, wherein the rotation angle is an angle by which the exercise appliance is rotated about the rotation axis from the time of starting the backswing to the predetermined timing.

15. The swing diagnosis apparatus according to claim 13, wherein the predetermined timing is a time at which the backswing transitions to a downswing.

16. The swing diagnosis apparatus according to claim 13, wherein the inclination of the ball hitting portion is an angle formed between an outer edge of a hitting surface of the ball hitting portion and a virtual straight line orthogonal to a target hit ball direction in a plan view.

17. The swing diagnosis apparatus according to claim 13, wherein the level is calculated according to a curved state of a hit ball predicted based on a relationship between the detected rotation angle and the detected face angle.

18. The swing diagnosis apparatus according to claim 13, wherein the level is calculated based on a speed of the ball hitting portion at impact.

19. The swing diagnosis apparatus according to claim 18, wherein the level is calculated according to the speed.

20. The swing diagnosis apparatus according to claim 13, wherein the calculated level is displayed.

21. The swing diagnosis apparatus according to claim 13, wherein the level is a score.

* * * * *